US010739362B2

United States Patent
Goemann-Thoss et al.

(10) Patent No.: US 10,739,362 B2
(45) Date of Patent: Aug. 11, 2020

(54) LABORATORY INSTRUMENT, SYSTEM AND METHOD FOR INSTRUMENT-CONTROLLED TREATMENT OF AT LEAST ONE LABORATORY SAMPLE USING AT LEAST ONE CONSUMABLE

(71) Applicant: Eppendorf AG, Hamburg (DE)

(72) Inventors: Wolfgang Goemann-Thoss, Hamburg (DE); Wolf Wente, Hamburg (DE); Andreas Thieme, Hamburg (DE); Jan-Gerd Frerichs, Norderstedt (DE); Christiane Markau, Hamburg (DE); Jan-Hendrik Hacker, Hamburg (DE)

(*) Notice: Subject to any disclaimer, the term of this patent is extended or adjusted under 35 U.S.C. 154(b) by 920 days.

(21) Appl. No.: 14/508,724

(22) Filed: Oct. 7, 2014

(65) Prior Publication Data
US 2015/0127270 A1    May 7, 2015

(30) Foreign Application Priority Data

Oct. 7, 2013 (EP) .................... 13004814

(51) Int. Cl.
*G01N 35/00* (2006.01)
*G01N 33/48* (2006.01)
*G01N 33/68* (2006.01)

(52) U.S. Cl.
CPC ....... *G01N 35/00584* (2013.01); *G01N 33/48* (2013.01); *G01N 33/68* (2013.01);
(Continued)

(58) Field of Classification Search
CPC .......... G01N 35/00584; G01N 35/00
(Continued)

(56) References Cited

U.S. PATENT DOCUMENTS

| 6,544,476 B1 | 4/2003 | Mimura et al. |
| 2002/0032762 A1 | 3/2002 | Price et al. |

(Continued)

FOREIGN PATENT DOCUMENTS

| EP | 0952452 A1 | 10/1999 |
| EP | 0973115 A2 | 1/2000 |

(Continued)

OTHER PUBLICATIONS

U.S. Appl. No. 14/508,703 (U.S. Publication No. US 2015-0125961 A1), entitled, "Laboratory instrument with access control device and method for instrument-controlled treatment of laboratory samples, laboratory instrument and method," filed on Oct. 7, 2014, of Goemann-Thoss, et al.

(Continued)

*Primary Examiner* — Christine T Mui
(74) *Attorney, Agent, or Firm* — Todd A. Lorenz

(57) ABSTRACT

The invention relates to a laboratory instrument, a system and a method for the instrument-controlled treatment of at least one laboratory sample using at least one consumable, by means of which information is obtained automatically as first data during a treatment, wherein the system and/or the laboratory instrument comprises a communication apparatus for establishing a data connection to at least one data processing apparatus, wherein the communication apparatus is suitable for transmitting these at least some first data to the data processing apparatus.

8 Claims, 5 Drawing Sheets

(52) U.S. Cl.
CPC .............. *G01N 35/00663* (2013.01); *G01N 2035/00881* (2013.01)

(58) Field of Classification Search
USPC .......................................................... 422/62
See application file for complete search history.

(56) References Cited

U.S. PATENT DOCUMENTS

| | | |
|---|---|---|
| 2002/0135678 A1 | 9/2002 | Bacus et al. |
| 2003/0141116 A1 | 7/2003 | Nuesch et al. |
| 2004/0171171 A1 | 9/2004 | Appoldt et al. |
| 2005/0014285 A1 | 1/2005 | Miller |
| 2005/0112542 A1 | 5/2005 | West |
| 2005/0131734 A1 | 6/2005 | Sugiyama |
| 2005/0159982 A1 | 7/2005 | Showalter et al. |
| 2005/0192908 A1 | 9/2005 | Jorimann et al. |
| 2006/0173575 A1 | 8/2006 | Lefebvre et al. |
| 2006/0242276 A1 | 10/2006 | Price et al. |
| 2007/0143465 A1 | 6/2007 | Gonzalez et al. |
| 2007/0233303 A1 * | 10/2007 | Naito .............. G01N 35/00584 700/108 |
| 2007/0255756 A1 | 11/2007 | Satomura et al. |
| 2008/0059472 A1 | 3/2008 | Yamamoto et al. |
| 2008/0256227 A1 | 10/2008 | Malin |
| 2010/0106427 A1 | 4/2010 | Fukuma et al. |
| 2010/0271479 A1 | 10/2010 | Heydlauf |
| 2011/0246215 A1 | 10/2011 | Postma et al. |
| 2013/0045473 A1 | 2/2013 | Duerr et al. |
| 2013/0159135 A1 | 6/2013 | Jones et al. |

FOREIGN PATENT DOCUMENTS

| | | |
|---|---|---|
| EP | 1248170 A1 | 10/2002 |
| EP | 1840576 A2 | 10/2007 |
| EP | 1981245 A1 | 10/2008 |
| EP | 2182364 A2 | 5/2010 |
| EP | 2182365 A2 | 5/2010 |
| EP | 2299277 A1 | 3/2011 |
| EP | 2450711 A1 | 5/2012 |
| WO | WO 1994011838 A1 | 5/1994 |
| WO | WO 2008012104 A2 | 1/2008 |
| WO | WO 2009085534 A1 | 7/2009 |
| WO | WO 2012/045415 A1 | 4/2012 |

OTHER PUBLICATIONS

U.S. Appl. No. 14/508,716 (U.S. Publication No. US 2015-0104796 A1), entitled, "System comprising at least two laboratory instruments for instrument-controlled handling of a partial problem in a treatment process containing treatments of at least one laboratory sample, laboratory instrument and method," filed on Oct. 7, 2014, of Goemann-Thoss, et al.

U.S. Appl. No. 14/508,722 (U.S. Publication No. US 2015-0105877 A1), entitled, "Configuration control device for a laboratory instrument, laboratory instrument with the configuration control device for instrument-controlled treatment of at least one laboratory sample and a method for configuring the laboratory instrument by means of the configuration control device," filed Oct. 7, 2014, of Goemann-Thoss, et al.

* cited by examiner

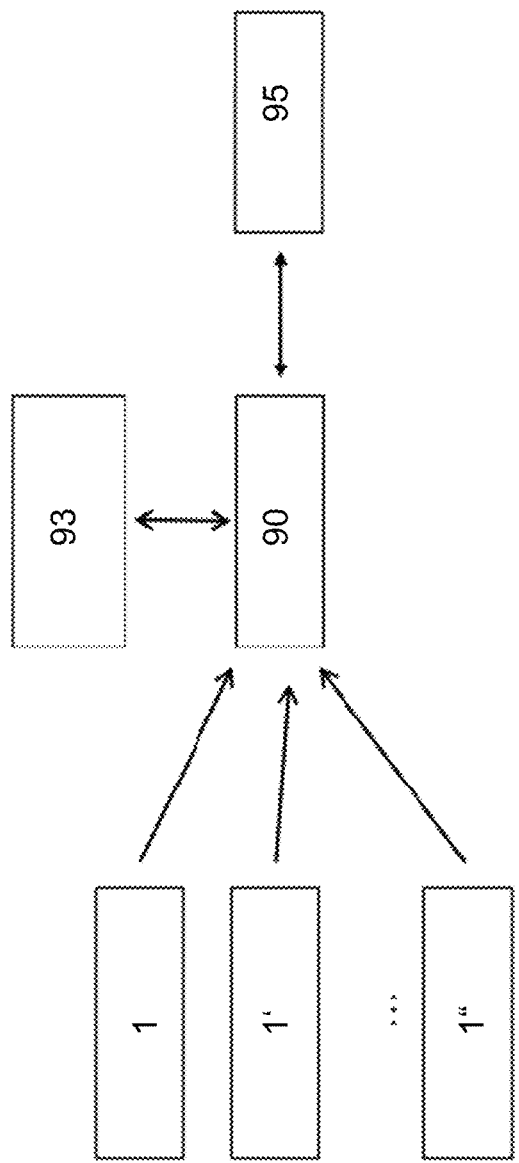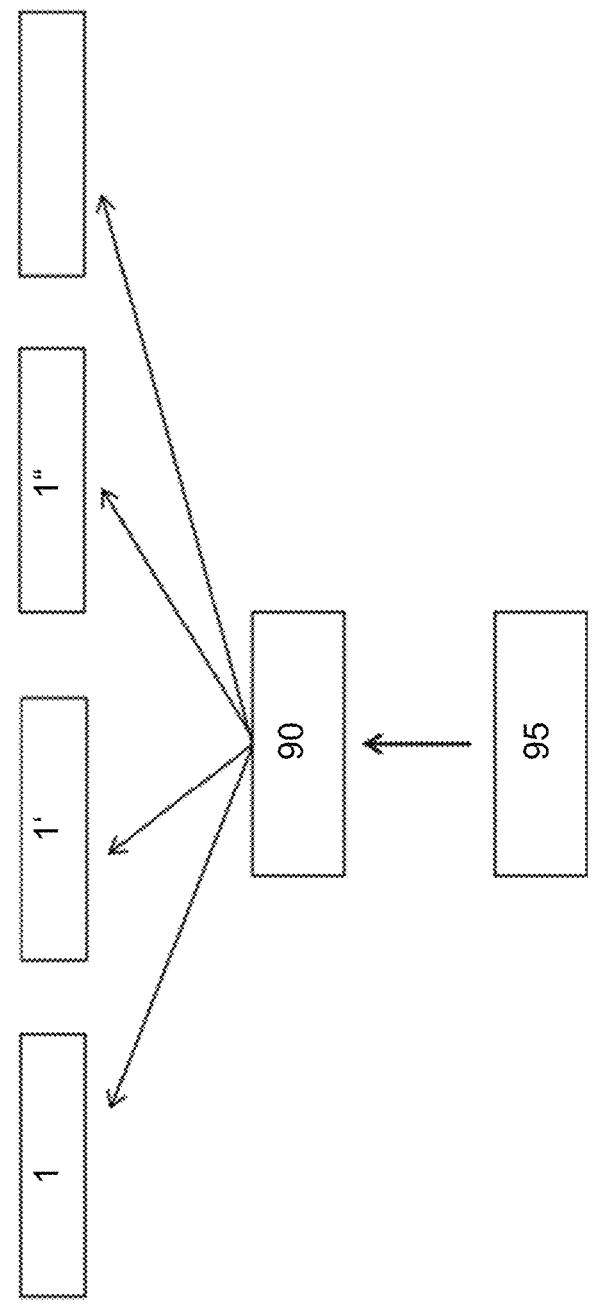

LABORATORY INSTRUMENT, SYSTEM AND METHOD FOR INSTRUMENT-CONTROLLED TREATMENT OF AT LEAST ONE LABORATORY SAMPLE USING AT LEAST ONE CONSUMABLE

The invention relates to a laboratory instrument, a system and a method for instrument-controlled treatment of at least one laboratory sample using at least one consumable.

Laboratory instruments are used in chemical, biological, biochemical, medical or forensic laboratories to handle laboratory samples, in particular liquid laboratory samples, with great efficiency. Such laboratory instruments at least partly automate treatment steps which would otherwise have to be performed manually and thus increase the speed, precision and reliability of these treatments. A treatment of laboratory samples, which are usually in liquid form, may be directed to modifying or examining these laboratory samples, in particular the composition thereof, in a physical, chemical, biochemical or other manner.

The aforementioned laboratory instruments comprise one or more treatment apparatuses for instrument-controlled treatment of the at least one laboratory sample using at least one consumable. They often have a program control, by means of which a user of the laboratory instrument can set the treatment to be performed by setting the desired program parameters and, as a result thereof, can influence the progress of a treatment. There are often a number of ways for obtaining treatment success. Different plans or procedures, which e.g. are undertaken by different users, may lead to the same results, i.e. to the same treatment. In particular, a different amount of one or more consumable can be used, depending on the plan. Such consumables can be sample containers, transport containers, such as e.g. capillaries, pipette tips or dispenser tips, cleaning means, etc. The program parameters are set by means of an operating unit of the laboratory unit, which enables the input and output of information, in particular of values of the program parameters. The treatment is performed in at least partly automated fashion. After the treatment has been completed, the user can continue to use the treated sample and the laboratory instrument is available for a further use. The subsequent user, who performs the next treatment, will use the laboratory instrument in a similar manner. The consumables required for performing this, in particular sample containers or transport containers, are usually distributed manually by the operating staff to the storage positions, provided for these, in the laboratory or on the laboratory instrument. An interruption of the workflow in a laboratory is regularly created if the amount of consumables required for filling the storage positions is unexpectedly no longer available in the laboratory. Laboratories often employ additional operating staff, who are responsible for the basic supply with consumables which are used during work with the laboratory instruments. Going beyond such strategies, the present invention pursues a different way for improving the situation.

It is an object of the present invention to make available a laboratory instrument, a system, and a method for instrument-controlled treatment of at least one laboratory sample using at least one consumable, by means of which the workflow in a laboratory can be improved.

The invention achieves this object by means of, in particular, the laboratory instrument and the methods claimed herein. Preferred embodiments of the invention are, in particular, the subject matter of the dependent claims.

The laboratory instrument according to the invention for the instrument-controlled treatment of at least one laboratory sample comprises: at least one treatment apparatus, which is configured to perform the treatment of the at least one laboratory sample using an amount of at least one consumable, and a control apparatus for controlling the treatment, comprising a data processing apparatus and a storage apparatus for storing data, wherein the control apparatus is configured to acquire, during at least one treatment performed by a treatment apparatus, at least one first item of information dependent on this treatment in first data, in particular by means of a counting, measuring or calculating process and to store at least some of the first data in the storage apparatus, wherein the laboratory instrument comprises a communication apparatus for establishing a data connection to at least one external data processing apparatus, and this communication apparatus is configured to transmit these at least some first data to the external data processing apparatus. The external data processing apparatus is not a component of the laboratory instrument according to the invention.

The invention provides for already automatically acquiring information about the consumables, in particular about the use and/or consumption thereof, during the use of the consumables and for making available the corresponding data as first data for the further handling in a further data processing apparatus. This further data processing apparatus can be a component of the system according to the invention or can, in particular, be a data processing apparatus disposed at a distance therefrom, which external data processing apparatus is, in particular, contacted by the communication apparatus of the laboratory instrument, e.g. by means of a remote data connection using the Internet. In the case of a system with an assemblage of a plurality of such laboratory instruments, consumable data can be collected centrally, e.g. on a server. As a result of these solutions according to the invention, it is possible to obtain consumable data, by means of which, in accordance with a preferred configuration of the invention, it is possible to provide an automatic ordering and/or supply system for consumables.

The "first data" can be information about the amount and/or the number of consumables, which are used up during the performed treatment or which were used up after a certain amount of time or within a certain time period, in particular after completion of the treatment. The first data contain the amount specification, preferably in each case with reference to the type of consumable used up. By denoting the type of consumable, unambiguous information, by means of which the consumable can be resupplied, should preferably be provided.

The first data contain the amount specifications, preferably in each case in a user-dependent manner. In this case in particular, it is preferable for the laboratory instrument or the system to comprise an access control device, by means of which a user can be identified.

A consumable is an article which must be disposed of after a single use because either cleaning and reuse is not possible or uneconomical or because the consumable has become unusable for use in a further treatment after use in a treatment. A consumable can be manufactured from plastic or comprise plastic. A consumable is preferably a sample container, also referred to as sample holder. A sample container can be a single container, e.g. a sample tubule, for example PCR vessels with different volumes (0.2 mL or 0.5 mL), Eppendorf vessels with different volumes (1.5 mL, 0.5 mL, 2 mL; 5 mL), Falcon® tubes with different volumes or a sample plate, or a multiple container, e.g. a microtitre plate (PCR plate), PCR tube strips, a cell culture microplate or a cell culture multi-well plate or else a storage box (carton) for sample tubules, which are conventional in freezers. A consumable is preferably a transport container, also referred to as a transport holder. By way of example, a transport container can be a capillary, cuvette, pipette tip or dispenser tip. A single-use container of a bioreactor (fermenter), which is also conventional in various volumes, is also a consumable. A consumable can also be a closure for a single container or a multiple container, for example a closure mat, a cover for a plate (microtitre, PCR; cell culture microplates and multi-well plates) or cap strips (linked caps for PCR tube strips). Consumables are stored in a packaged manner, wherein a plurality ($\leq 10$) or multiplicity ($>10$) (predetermined amount) of consumables are contained in a single package. Since various types of consumables are used during routine laboratory operation, all types always have to be kept in stock. Therefore, this storage of various consumables requires large spatial requirements since it is not a single consumable that needs to be stored, but usually a plurality or multiplicity thereof.

The control apparatus of the laboratory instrument is preferably configured to acquire, during at least one treatment performed by a treatment apparatus, at least one first item of information dependent on this treatment, in particular by means of a counting, measuring or calculating process In the case of a pipetting process by means of one or more pipette tips, dispenser tips or capillaries which may be fastened to a pipetting tool head of a laboratory instrument, in particular of a laboratory machine, it is possible, in particular, to register and/or count each disposal of these consumables and/or store the corresponding number. Furthermore, the laboratory instrument can comprise a sensor, by means of which a wear value of a consumable can be measured. In the case of a transparent cuvette, it would be possible, in particular, to measure the transmission through the empty cuvette as a wear value. If a consumable has an empirical value for the maximum number of possible uses of the consumable, it is possible, in particular as a wear value, for the maximum number of uses to be registered.

In particular, the data connection that can be established by means of the communication apparatus can be a remote data connection which is established, in particular, via a world-wide network, in particular via the Internet. The data processing apparatus can be an external data processing apparatus which, in particular, is disposed outside of the laboratory in which the laboratory instrument is positioned.

An—in particular external—data processing apparatus can be a computer or microprocessor or can have a computer or microprocessor. The data processing apparatus can, in particular, be a server. A server is, in particular, a computer, the hardware of which is preferably tuned to server applications. Preferably, the system according to the invention comprises at least one data processing apparatus, which is also referred to as external data processing apparatus belonging to the system. The latter is, in particular, not a component of the laboratory instrument.

An—in particular external—data processing apparatus preferably comprises in each case: at least one storage apparatus for volatile or permanent storage of data; at least one control apparatus; at least one communication apparatus; at least one interface apparatus.

In particular, the control apparatus is an electronic control apparatus. Within the scope of the present invention, a control apparatus generally comprises, in particular, a data processing apparatus, in particular a computer unit (CPU) for processing data and/or a microprocessor. A computer unit is preferably also configured for controlling the external data processing apparatus and/or the treatment process and/or the individual treatments.

A communication apparatus is preferably configured for the transmission and/or reception of data, in particular the data interchange via a data connection provided by the communication apparatus, in particular a remote data connection to a remote instrument. In particular, the instrument arranged at a distance from a laboratory instrument is also referred to as "remote instrument" or external instrument. In particular, a data processing apparatus which is not a component of a laboratory instrument is also referred to as an external data processing apparatus. The data connection, in particular the remote data connection, can be established over a restricted network of computers (in particular an intranet) or over a worldwide network of computers (in particular the Internet). The data connection, in particular the remote data connection, can also be established over a wireless connection. The data connection, in particular the remote data connection, can, in particular, be established over a mobile communications connection.

An—in particular external—data processing apparatus preferably comprises at least one storage apparatus, in which first and/or second data can be stored.

The laboratory instrument, in particular the system, preferably comprises at least one user interface apparatus.

Preferably, the data processing apparatus of the laboratory instrument or of the system is a computer or microprocessor or comprises a computer or microprocessor. The data processing apparatus can be a server. The data-processing apparatus can comprise a booking database. The latter can comprise a calendar in the form of calendar dates, in which entries of temporal use of one or more laboratory instruments can be entered with a certain temporal accuracy, e.g. with occupation down to minute accuracy. Preferably, the system is configured to manage the use of one, some or all laboratory instruments of the system by means of the booking database. Accordingly, the entries in the booking database can have been brought about, firstly, by the computer or, secondly, been entered by one or more users.

Preferably, a laboratory instrument, or the system, comprises, in particular, a planning apparatus for planning an expected consumption of consumables. The planning apparatus is preferably realized by the data processing apparatus of the system or of the laboratory instrument. To this end, preferably, a system or a laboratory instrument, in particular an—external—data processing apparatus—belonging to the system—is configured to determine an amount of consumables, taking into account the booking data stored in the booking database, in particular the information contained, which relates to the temporal booking of one or more laboratory instruments. Here, it is possible, in particular, to take into account the planned treatment, in particular the type of treatment, for which the instrument was booked. In particular, the usage can be different for every possible type of treatment in a laboratory instrument. Preferably, the laboratory instrument or the system is configured to uniquely assign an amount of consumables per period of time and/or per treatment to the reservation data, or to estimate this. This amount of consumables can be calculated or derived from tables, in which the values corresponding to the calculations are stored. The established amount of consumables can be compared to one or more storage numbers, which represent the amount of consumables respectively stored. From this, the laboratory instrument or the system can establish which additional need for consumables exists during the period of time considered. The requirement for consumables can be transmitted as "first data" to an external data processing apparatus via a remote data connection. The external data processing apparatus can be assigned to a provider of the consumables. On the basis of the first data, the provider can plan a delivery or an offer for the amount of consumables required. As a result, the workflow in a laboratory is improved further.

Preferably, the planning apparatus is embodied to store and evaluate planning data, by means of the use of which it is possible to plan an expected consumption of consumables. Preferably, the planning apparatus is embodied to collect information about performed treatments as first data and, in particular, to establish, in particular calculate, at least one statistical variable as a function of the first data. This statistical variable can be a sum of the used amounts of at least one consumable, can be a mean value, can, in particular, be such a sum related to a type of treatment, related to a laboratory instrument or to a specific type of laboratory instrument, related to a system according to the invention, related to a user, related to a period of time, in particular as a function of weekdays, work days and/or holidays and/or related to at least one further reference variable or item of information.

Preferably, the planning apparatus is embodied to store and evaluate planning data, by means of the use of which it is possible to plan an expected consumption of consumables, taking additional account of booking data. By using a statistical variable, which was established as a function of a reference variable, it is possible to establish an expected consumption of consumables in combination with booking data, which are likewise dependent on the reference variable. By way of example, it is possible to combine the mean use for a specific treatment, e.g. a sample serial dilution in at least one laboratory machine, which is known from the planning data, with the booking data, which specify the booking of the at least one laboratory machine for a specific period of time, e.g. one week. From this, the planning apparatus can establish the expected consumption, for one week, of the consumables associated with this type of treatment and can provide this value as "first data", in particular transmit the latter to an external data processing apparatus. In another example, the planning apparatus can establish the consumption values for a specific user to be expected with reference to a future period of time, by virtue of using planning data which contain historical, stored specifications about consumed amounts of consumables by treatments of the specific user, preferably as a function of the type of treatment. The future period of time can relate to booking data, i.e. take place as a function of treatments planned in actual fact by a specific user. However, the planning apparatus can also establish an expected future value for the consumption of consumables by this user from statistical, historical consumption values of this user, in particular without taking into account booking data.

Preferably, the planning apparatus is configured to collect, in particular store, the first data provided by one or more laboratory instruments, which first data were, in particular, acquired by the one or more laboratory instruments during one or more treatments of laboratory samples.

Preferably, the planning apparatus is configured to determine at least a first amount X of a consumable Y from the collected first data. Preferably, the planning apparatus is configured to store third data storing predetermined information about a second amount—this amount is denoted by "N"—of the consumable Y. Preferably, the planning apparatus is configured to compare the amount X with the amount N, in particular in order to determine a need for consumables. Preferably, the communication apparatus is configured to transmit the information about the stored amount "N" as these at least some first data to the—in particular second—external data processing apparatus, particularly if the comparison of the amount X with the amount N results in a need of the amount "N" for the consumable "Y", in particular if X>=N or if it is determined that X>=N is to be expected at a specific time. Here, it is possible, in particular, also to take into account the expected consumption of the consumable "Y" in accordance with a booking schedule, as already described previously. The aforementioned preferred configuration of the planning apparatus is particularly advantageous if consumables are stored in predetermined amounts for use with the laboratory instrument or with the system and/or can be ordered for use with the laboratory instrument or with the system, wherein this predetermined amount, in particular, corresponds to the amount N, which is stored in the planning apparatus.

Preferably, a data processing apparatus of the laboratory instrument is configured to receive user data which a user transmits to the receiving data processing apparatus of the laboratory instrument, in particular with the aid of an external data processing apparatus, in particular via a communication apparatus of this external data processing apparatus or via an interface apparatus of this external data processing apparatus.

It is preferable for the laboratory instrument to transmit the provided and/or generated first and/or second data to the—in particular external—data processing apparatus, in particular the server, in a direct manner, i.e. via a direct wireless or wired data connection, in particular a remote data connection, to the—in particular external—data processing apparatus, in particular the server. It is also preferable for the laboratory instrument to transmit the provided and/or generated first data to the—in particular external—data processing apparatus, in particular the server, in an indirect manner, i.e. non-direct manner, i.e. via an indirect wireless or wired data connection, in particular a remote data connection, to the—in particular external—data processing apparatus, in particular the server. Here, at least one further data processing apparatus, which receives and forwards the first and/or second data, can be interposed. This further data processing apparatus can be a laboratory apparatus or the control apparatus thereof, or a different data processing apparatus, in particular a server.

The external data processing apparatus can be configured to generate the second data from the received first data. The system according to the invention or a laboratory instrument according to the invention and/or, preferably, the external data processing apparatus can be configured, in particular, to start an ordering process for consumables depending on the first data. To this end, the external data processing apparatus can transmit at least second data, preferably to the system according to the invention or to the laboratory instrument for confirming receipt of the first data, which system or laboratory instrument transmitted the first data and now receives these second data.

Every user can establish a first data connection with the access control device by means of the same user interface apparatus or a plurality of users can establish a first data connection with the access control device by means of different user interface apparatuses. A user interface apparatus can be a component of the access control device. An access control device can be a component of the user interface apparatus. A user interface apparatus can be a component of a laboratory instrument. A user interface apparatus preferably comprises in each case: a control apparatus for a user interface apparatus; a communication apparatus for establishing a data connection to a laboratory instrument by means of an interface apparatus of same; an input apparatus for acquiring user inputs of a user; an output apparatus, in particular an indication unit and/or a display, for outputting information to the user. Here, the control apparatus of the user interface apparatus is preferably configured to interchange data with the laboratory instrument via the data connection, which data were obtained from the user inputs and, in the laboratory instrument according to the invention, cause the user to be granted authorizations and/or access permissions on the laboratory instrument according to the invention, wherein a simultaneous log on and/or the simultaneous access of a first and at least a second user on the laboratory instrument according to the invention with respectively assigned access permissions to functions of the laboratory instrument can be controlled via the interface apparatus.

A user-dependent procedure refers to the fact that a method is followed either dependent on a user, in particular a class, group or role of the user, which can be distinguished by various aspects, or in a user-individual manner. A user-dependent display on the user interface means, in particular, that use is made of a specific user interface, in particular a request mask, which is assigned to said user.

The user class or role can be established by means of a database. For an individual, the user class can emerge from his specialist qualification, his professional standing in the company or else by the assignment according to a different criterion. The criterion can also be bound to a measurement which is performed by at least one sensor that is signal connected to the control apparatus and can be a component of the laboratory machine. This measurement can, in particular, determine a personalized measurement parameter, in particular establish a body parameter of the person. As a result of this information it is possible, in particular, to adapt the laboratory instrument to the body dimension, e.g. to the body height of the person, in order, for example, to adapt the setting of the laboratory instrument automatically to this body dimension. This can result in improved ergonomics. The sensor can also comprise a microphone, by means of which the speech of the user is acquired, in particular recorded. The speech data can be used and/or evaluated for generating a log file. Preferably, the configuration control device, in particular the control apparatus thereof, comprises a speech recognition apparatus. The speech acquired by the sensor can be analysed and evaluated by means of the speech recognition apparatus, with speech data being established. The speech data can be used to acquire a control command, by means of which the control of the laboratory instrument and/or of the configuration control device can be influenced. In particular, the speech data can be evaluated in order to establish the speech of the user. The user interface can be adapted as a function of the speech, by virtue of the text displayed on the user interface and/or the speech output by means of a loudspeaker of the laboratory instrument being adapted to the speech established by the speech analysis.

An interface apparatus serves for connecting two apparatuses which can each process, in particular transmit and/or receive, signals, in particular information, in particular data. An interface apparatus can contain at least one hardware interface and/or at least one software interface.

Hardware interfaces are, in particular, interfaces between electrically operating units in accordance with the usual understanding in electrical engineering and electronics. Presently, the phrase "hardware interface" in particular also denotes the connection components between at least two electrically operating units themselves, i.e., in particular, all constituents which enable this connection, e.g. integrated circuits, electronics and lines, by means of which electrical signals are transmitted between the at least two electrically operating units. In particular, these two electrically operating units can be a laboratory instrument and an external data processing apparatus or two laboratory instruments, or two electrically operating units, within a laboratory instrument. A hardware interface need not, but can, comprise a detachable connection apparatus for releasing and/or re-establishing this connection, in particular at least one connector.

Software interfaces, in particular software-side data interfaces, are, in particular, logical connection points in an information management system, in particular a software system: they enable and regulate the interchange of commands and data between various processes and components. Software interfaces may be data-oriented interfaces used for communication purposes only. In this case, the software interface merely contains information which is interchanged between involved system parts.

The aforementioned preferred embodiments of a laboratory instrument according to the invention also apply to a laboratory instrument which is a component of the system according to the invention.

Preferably, in a first configuration of the laboratory instrument, the communication apparatus of the laboratory instrument or of the external data processing apparatus belonging to the system is configured to receive a communication request which was transmitted to the communication apparatus by an—in particular second—external data processing apparatus. Thus, communication for data interchange can be started, i.e. initiated, firstly, by the laboratory instrument and/or by the system according to the invention, but it can also be initiated by an—in particular second—external data processing apparatus which, in particular, is not a component of a laboratory instrument or of the system. Similar techniques are referred to as "push technology" in the field of mobile communication technology. A "push" or "server push" describes, in particular, an Internet-based type of communication between data processing apparatuses, in which the request is initiated after a predetermined transaction by a central server or the publisher of information. Usually—not least due to the basic right of self-determination of the persons or legal entities owning the data processing apparatuses—the initiative lies with the individual client. However, the push technology enables the transmission of information to the clients via an information channel, which after a preceding agreement with the client, who has consented, in particular the "request" of whom for receiving "push" information via this information channel.

Preferably, in a second configuration of the laboratory instrument, which comprises the first configuration, the communication apparatus of the laboratory instrument or of the external data processing apparatus belonging to the system is configured to permit a remote data connection on the basis of the communication request by the—in particular second—external data processing apparatus, said remote data connection being established between the—in particular second—external data processing apparatus and the communication apparatus. Here, the remote data connection initiated by the—in particular second—external data processing apparatus forms an information channel, by means of which the—in particular second—external data processing apparatus transmits second data to the communication apparatus. The second data can be dependent on the first data and can, in particular, relate to an amount of at least one consumed consumable. The second data can represent product information, in particular information about laboratory instruments or consumables, or confirmation information about started ordering processes which, in particular, are started dependent on the first data.

Preferably, in a third configuration of the laboratory instrument, which comprises the second configuration, the control apparatus or the data processing apparatus of the laboratory instrument according to the invention and/or the external control apparatus belonging to the system is configured to process the second data automatically.

Preferably, in a fourth configuration of the laboratory instrument, which comprises the second or third configuration, the laboratory instrument or the system according to the invention comprises a user interface apparatus with an indication apparatus. Preferably, the control apparatus or the data processing apparatus of the laboratory instrument or of the system according to the invention is configured to obtain second items of information from the second data and to indicate these second items of information to the user on the indication apparatus of the user interface apparatus.

Preferably, in a fifth configuration of the laboratory instrument which, in particular, can comprise the first, second, third or fourth configuration, the control apparatus or the data processing apparatus of the laboratory instrument or of the system according to the invention is configured to control the communication request from the—in particular second—external data processing apparatus, in particular to permit the remote data connection, as a function of the first data and/or as a function of other conditions.

Preferably, in a sixth configuration of the laboratory instrument which, in particular, can comprise the first, second, third, fourth or fifth configuration, the system according to the invention or the laboratory instrument comprises an access control device configured to control the access, in particular the communication request, of the—in particular second—external data processing apparatus, in particular to grant or deny access.

Preferably, in a seventh configuration of the laboratory instrument which, in particular, can comprise the first, second, third, fourth, fifth or sixth configuration, the control apparatus of the laboratory instrument and/or the external data processing apparatus belonging to the system of the system according to the invention or the data processing apparatus of the laboratory instrument is configured to acquire, during at least one treatment, at least one first item of information about the variable X as a function of Y, in particular by counting or measuring, wherein the values X and Y characterize at least one consumable Y of the amount X, and to acquire this at least one first item of information in the first data. The amount X can e.g. represent a number and/or a volume and/or a mass.

Preferably, in an eighth configuration of the laboratory instrument which, in particular, can comprise the first, second, third, fourth, fifth, sixth or seventh configuration, the system and/or the laboratory instrument comprises a user interface apparatus and an access control device, which is configured to control, in particular to permit, the access of at least one user, i.e., for example, an individual, a group, an administrator, a buyer or another rights holder, accessing via the user interface apparatus and to identify this user in the process. Preferably, the control apparatus of the laboratory instrument or the external data processing apparatus belonging to the system is configured to acquire the first data as a function of the identified user and/or to acquire the information relating to the identified user, in particular user data, as a component of the first data.

Preferably, in a ninth configuration of the laboratory instrument which, in particular, can comprise the first, second, third, fourth, fifth, sixth, seventh or eighth configuration, the control apparatus of the laboratory instrument or the external data processing apparatus belonging to the system is configured to acquire the first data as a function of, additionally, another condition, in particular as a function of a type of treatment, etc.

Preferably, in a tenth configuration of the laboratory instrument which, in particular, can comprise the first, second, third, fourth, fifth, sixth, seventh, eighth or ninth configuration, the control apparatus of the laboratory instrument or the external data processing apparatus belonging to the system is configured to establish, in particular calculate, the first data as a function of at least one planned treatment, in particular as a function of at least one treatment planned in accordance with the booking data from a booking database.

The invention furthermore relates to a system, comprising at least one laboratory instrument according to the invention and at least one external data processing apparatus belonging to the system, in particular a server, which are interconnected for interchanging of data, in particular configuration data. Here, the communication apparatus of the at least one laboratory instrument is preferably configured to establish a data connection with the at least one external data processing apparatus belonging to the system in order to transmit these at least some first data to the external data processing apparatus belonging to the system. To this end, the external data processing apparatus belonging to the system preferably likewise comprises a communication apparatus. The system is, in particular, configured in such a way that a data connection can be established between the at least one external data processing apparatus belonging to the system and the at least one laboratory instrument, by means of which data connection the first data and/or the second data can be interchanged. Such a system renders it possible to collect at least the first data in the system, in particular to collect these over a period of time. The collected first data can then be processed further; in particular, the first data and/or the information contained in the first data can be transmitted to a second external data processing apparatus. By way of example, the system can be disposed in a laboratory by virtue of the first data, in particular consumption information, being collected by one or more laboratory instruments of the system by means of the system. The second external data processing apparatus can be a server outside of the laboratory, to which the system transmits the first data and/or the information contained therein, e.g. by means of a remote data connection using the Internet.

Preferably, in a first configuration of the system, the at least one external data processing apparatus belonging to the system comprises a storage apparatus and is, in particular, configured to process the first data and/or the second data, in particular to store these in said storage apparatus.

Preferably, in a second configuration of the system, the system, which can, in particular, comprise the first configuration, or the external data processing apparatus belonging to the system comprises a communication apparatus for establishing a remote data connection to at least one second external data processing apparatus in order to transmit these at least some first data to the second external data processing apparatus by means of this remote data connection. The second external data processing apparatus is preferably not a component of the system.

The aforementioned configurations of the laboratory instrument according to the invention and/or of the system according to the invention may be combined with other features mentioned within the scope of the description of the present invention.

In a laboratory instrument, the access control device enables the access of one or more further users to the laboratory device to be controlled when a first user is already logged on and the session of said first user is still running on the laboratory instrument, i.e. when the access of the further user is still active. As a result of this embodiment, the laboratory instrument can be used more efficiently and the productivity of the laboratory can be improved.

Within the scope of the present invention, a control apparatus generally comprises, in particular, a data processing apparatus, in particular a computer unit (CPU) for processing data and/or a microprocessor, or said control apparatus is a data processing apparatus. The computer unit of the control apparatus of a laboratory instrument is preferably also configured for controlling the treatment process and/or the individual treatments.

The control apparatus of the laboratory instrument and/or the optional access control and/or the optional user interface apparatus—in particular all of these—can be integrated in a physical instrument unit but can also in each case be independent physical instrument units. A physical instrument unit can, in particular, be a module which is or can be connected to the laboratory instrument. The control apparatus of the laboratory instrument and/or the optional access control device and/or the optional user interface apparatus or components of these components can also be implemented by software functions or can, in particular, be available as program code. By way of example, a laboratory instrument can comprise a computer which, in combination with software functions, in each case at least partly implements the control apparatus of the laboratory instrument and/or the optional access control device and/or the optional user interface apparatus. By way of example, if the access control device is integrated into the laboratory instrument, the access control device itself may be part of the control apparatus of the laboratory instrument or be implemented by means of the control apparatus, in particular by software functions, in particular at least partly as executable program code.

A module can, in particular, comprise the access control device and/or the configuration control device and/or a user interface apparatus. A module is an instrument which is separate from other instruments and/or an instrument which can be separated from the other instrument, in particular the laboratory instrument. A laboratory instrument may comprise a connection apparatus, by means of which the module can be connected to the laboratory instrument, in particular by means of a connection which is detachable by the user. A module may be portable, i.e. transportable by a user. The module can also be securely connected to the laboratory instrument. The modular design offers advantages during the production of laboratory instruments. A portable module offers greater flexibility when using a laboratory instrument.

Preferably, the external data processing apparatus belonging to the system comprises a computer unit.

Preferred embodiments of the access control device and of the laboratory instrument with this access control device are mentioned within the description of the present invention or can be gathered therefrom.

The access control device is preferably configured to control the request of the at least one further user in respect of logging onto the access control device, in particular to control the access to at least one function of the laboratory instrument, in particular to grant the request (access granted) or to reject the request (access denied), during the session of the first user.

The access control device is an apparatus configured for data processing. It serves for access control. The access control device comprises a control apparatus. The control apparatus is embodied for data processing. In particular, the control apparatus is an electronic control apparatus. It preferably has a data processing apparatus which, in particular, is electronic.

The data processing apparatus preferably comprises a computer unit, in particular a CPU, furthermore preferably at least one data storage apparatus, in particular for volatile and/or permanent storage of data. The data processing apparatus is preferably embodied to establish one or more first data connections to one or more user interface apparatuses, which can, in particular, be components of the access control device or of the laboratory instrument, by means of the first interface apparatus; preferably to establish a second data connection to the laboratory instrument via the second interface apparatus; and preferably to control access permissions for the access of users via the user interface apparatuses and the first and second data connections to functions of the laboratory instrument; wherein, preferably, the access permissions can be controlled in such a way that simultaneous access (being logged on) of a first and at least one further user occurs with in each case separately assigned access permissions to functions of the laboratory instrument.

A data connection connects, in particular, two data-processing units, in particular two data processing apparatuses, in such a way that data can be interchanged, either unidirectional or bidirectionally, between the units. The data connection can be realized with, or without, cables, in particular as a wireless connection. A remote data connection connects, in particular, two data processing units, in particular two data processing apparatuses, which are arranged at a distance from one another, which are therefore, in particular, not components of the same instrument, in particular of the same configuration control device, access control device, user Interface apparatus or of the same laboratory instrument if the aforementioned instruments are embodied as separate instruments. A data connection, in particular a remote data connection, from one instrument to another instrument is preferably realized by a direct connection between the two instruments or by means of an indirect connection between the two instruments such that a third instrument is switched between the two instruments in order to forward the data. In particular, a remote data connection can be realized via a network of computers, in the case of which the instruments connected via the remote data connection are connected via the network. The network can be a restricted network, e.g. an intranet, or a world-wide network, in particular the Internet.

The access control device is preferably configured to control the access permissions by virtue of the control apparatus using a data connection to a database for access permissions. The database for access permissions is preferably stored in at least one, preferably in exactly one, storage apparatus for access permissions. The at least one storage apparatus for access permissions can be disposed in the access control device and/or it can be disposed in an external data processing apparatus. "External" means that the instrument, in this case the data processing apparatus, is not a constituent of the device in question, in this case the access control device. The database for access permissions can be stored centrally, but it can also be stored in a plurality of storage apparatuses which can each have some of the data in the database or else have a copy of the data in the database.

An—in particular second—external data processing apparatus can be a computer, in particular a server, which is configured for establishing a data connection to more than one access control device and/or to more than one laboratory instrument. An—in particular second—external data processing apparatus can comprise a computer or microprocessor. A server is, in particular, a computer, the hardware of which is preferably tuned to server applications. An external data processing apparatus can be a server, which communicates with the laboratory or system according to the invention via, in particular, the Internet. An external data processing apparatus can be a mobile data processing apparatus, which is configured for establishing a wireless data connection, in particular a data connection via a restricted computer network, in particular an intranet, or a world-wide computer network, in particular the Internet. A computer network is a combination of various technical, primarily independent, electronic systems (in particular computers, but also sensors, actuators, agents and other radio components, etc.), which combination enables the communication between the individual systems.

The laboratory instrument, the control apparatus of the laboratory instrument or the control apparatus of the optional access control device can comprise a communication apparatus for establishing a data connection to an external data processing apparatus, in particular via an interface apparatus of the laboratory instrument. The access control device is preferably embodied to establish the access permissions using the data connection to the external data processing apparatus, in particular via an interface apparatus of the access control device. The external data processing apparatus, belonging to the system, preferably comprises at least part, or all of, the database for access permissions.

The access control device, in particular a control apparatus of the access control device, is preferably configured to control authorizations and/or access permissions for the access of users via the user interface apparatuses and the first and second data connections to functions of the laboratory instrument. As a result of this, a user-dependent use of the laboratory instrument is possible, which is controlled depending on the respectively allocated access permissions. In particular, simultaneous use of the laboratory instrument by at least a first and at least a second user is made possible.

The access control device performs the access control. The phrase "access control" denotes, in particular, methods for managing the requests for resources and/or data, which are managed by an information management system and which are handled for managing the decisions as to how the request is handled, in particular whether or not access is granted and/or in what manner the access is or is not granted. In particular, the information management system can be an operating system which is executed on the access control device. If the user of an information management system wishes to perform a specific operation on a specific resource and/or on specific data, the access control device makes a decision as to whether this request should in actual fact be granted or whether it should be denied. An access control decision (yes/no) relates to, in particular, an access control triple consisting of "subject", "object" and "operation".

In particular, an active entity of a system, wishing to perform a specific operation on a specific object, is referred to as a subject. In this context, an entity denotes a uniquely determinable unit, relating to which information is to be stored and/or processed. The unit may be material or immaterial, concrete or abstract. Subjects are, in particular, human users of an information management system or computer programs which are used by human users for completing tasks. A subject may also be a group of users, e.g. laboratory worker, servicing technician, administrator. Accordingly, the group combines a plurality of individual subjects.

A user may represent an individual, or a group of a plurality of individuals, or a class of individuals, which were selected in accordance with a class rule or role rule.

The access control device can preferably distinguish between the at least one first user and the at least one second user. A user is preferably uniquely identified by the access control device. To this end, the access control device preferably processes identification data. The access control device is preferably embodied to authenticate the requesting user, i.e. to perform a verification method, by means of which the authenticity of the requesting user is checked and the user is authenticated if the verification is positive. By way of example, authentication data contain a login text and a password text or a data set for facial recognition or for an iris scan or for a fingerprint scan, etc. Furthermore, authentication can be performed by means of an RFID chip or NFC chip, or via gesture identification. In particular, an authentication may be performed in situ by means of direct access to the laboratory instrument or the access control device thereof, or by means of remote access.

The access control device preferably comprises an information management system, by means of which the access control is realized. The information management system is preferably an operating system of a laboratory instrument and/or an operating system of the access control device of a laboratory instrument, by means of which the access control device and/or the laboratory instrument are operated.

The access control device is preferably embodied to log the requesting user, in particular a plurality of requesting users, in particular the at least one first user and the at least one second user, onto the access control device, in particular onto the information management system of the access control device. The log-on process is also referred to as logging in. The successfully logged-on user preferably receives predetermined authorizations and/or access permissions. The user himself can cancel being logged-on or this can be cancelled by other conditions, for example by the instrument-controlled logging-off of the user, in particular if a maximum logged-on time, during which the user was logged-on, without interruption, via the access control device is exceeded, or after a predetermined time of inactivity, or depending on the time of the end of the treatment performed by the user or due to individual process programming. Cancelling of logging on preferably means that the authorization granted during the log-on is revoked.

Logging into the information management system is preferably brought about by virtue of the user being authenticated. After authentication, the user obtains, for logging-in purposes, a personalized access to the information management system, with authorizations and/or access permissions, which are established by means of the database for access permissions. A session starts with the login and it is terminated by logging out, which is also referred to as logging off.

The access control device is preferably embodied to release the use of, i.e. authorize the authenticated user to use, the authorizations, operations and objects on the laboratory instrument or the functions and services of the laboratory instrument, which comprises the access control device, as a function of the predetermined access permissions. The access control device is preferably software controlled, in particular program controlled. LDAP (Lightweight Directory Access Protocol) is preferably used as application protocol when implementing the software functions.

During access or attempted access, an object refers to, in particular, a passive entity on which an operation is to be performed. Objects are also referred to as "resources". Objects may be e.g.: data or data collections, i.e. files, data objects in databases, e.g. tables or columns, services or functions, in particular those services or functions which can be performed by the access control device and/or the laboratory instrument. By way of example, such services may denote the making available of a calendar database, wherein this use may provide the display of calendar dates, the read permissions and/or write permissions on the calendar database. By way of example, such services and functions may denote a notification function, by means of which it is possible to send notifications to the users, which notifications may, in particular, contain information about the availability of the laboratory instrument during a specific calendar time period. In particular, making it possible for treatment to be performed, which, in particular may contain the granting of the access permissions required for this, would also be such a function. By way of example, a function may be the switching-on of the UV illumination of the laboratory instrument or the opening of a housing door of a laboratory instrument housing.

Processes carried out on an object are referred to as operations. In particular, operations can be functions, in particular functions of the access control device or of the laboratory instrument. A plurality of functions can be performed on one object. If the object is a file, possible operations are writing, reading, adding, modifying, copying or deleting data. If the object is a service or a function, performing may be the only possible operation. The number of possible operations depends on the type of the object. The number of operations which can be performed by individual subjects on the same object may differ.

A specific object in combination with the specific operation is, in particular, referred to as an authorization. By way of example, a "read authorization" can be understood to be the combination of the operation "read" with the object "file", while e.g. an "execution authorization" can be understood to be the operation "execute" with the object "function".

In particular, the access control can be formulated as a permission function, formally described by permission_for(subject, object, operation)→(yes, no)

If this function is applied to the triple of parameters (subject, object, operation), the permission function returns either "yes" (access granted) or "no" (access denied).

In this permission function, it is also possible to provide a further input parameter which supplies a further condition for the access decision. By way of example, this condition can denote the purpose for which a specific access should take place. Furthermore, it is possible that the permission function returns not—or not only—the yes/no decision about the access permission, but also a condition (also referred to as "obligation"), as a function of which a decision is made about the access permission. In particular, this allows "permission with conditions" to be defined. In particular, such an obligation is already satisfied before the access or access attempt, but may also be satisfied during—or after—the access or the operation to be permitted.

The access control can take place in accordance with one or more specific data models. One such specific data model is, in particular, the access control model (ACM). In particular, the access control may comprise a so-called reference monitor. In particular, this component should be understood to be the functional core of the access control device. The reference monitor fulfils the function of deciding whether the access to an object, as desired by a subject, is granted. The access control device may preferably not release any access to a resource of the laboratory instrument without the reference monitor being used. The reference monitor preferably also satisfies the function of recording access attempts that took place.

The database about access permissions preferably contains information in the form of data about which operations are available for an object, in particular as a function of a specific time or time period. In particular, this renders it possible to set whether the access to the at least one treatment apparatus is granted to a user at a specific time and/or during a specific period of time, in particular whether the permission for starting on modifying a treatment on the laboratory instrument has been allocated at a specific time or in a specific time period, wherein the laboratory instrument is or can be connected to the access control device by means of the second data connection.

The database about access permissions preferably contains information in the form of data relating to which authorizations can be allocated to the requesting user, in particular as a function of possible permissions due to belonging to a group and/or belonging to a role.

The access control is preferably configured in accordance with one, or else in accordance with more, of the known basic forms DAC ("Discretionary Access Control"), MAC ("Mandatory Access Control") or RBAC ("Role-Based Access Control"), with RBAC being particularly preferred.

The RBAC model provides for individual subjects not to be assigned permissions directly, but rather indirectly by means of so-called "roles". A possible standard of the RBAC model, which can be applied within the scope of designing the access control device, is described in detail in US standard ANSI INCITS 359-2004. The access control device may be embodied at least partly as a RBAC model, in particular at least partly in accordance with the aforementioned US standard.

Preferably, the access control provides the use of at least one role, preferably of a plurality of roles, wherein, in particular, permissions are in each case combined within the role. The at least one role is preferably stored in the database for access permissions. In particular, a role is suitably adapted to a responsibility or a problem description within the scope of using a laboratory instrument, in particular within the business using the laboratory instrument and/or in the business which fulfils a servicing contract relating to the laboratory instrument by virtue of e.g. performing diagnostic functions on the laboratory instrument, and/or in the manufacturer of the laboratory instrument, which e.g. transmits firmware updates, calibrations or information about the laboratory instrument and/or the accessories thereof directly to the laboratory instrument via the access control device. In particular, such roles can combine permissions. Instead of storing a set of individual rights for each user, the latter can be assigned at least one role. The role assignment is particularly reliable in terms of the implementation and requires relatively little outlay, in particular management outlay when establishing and storing permissions.

The access control preferably provides for at least two, preferably a plurality of, roles. Possible roles are, in particular, administrator ("Admin"), maintenance, normal laboratory user ("LabUser"), inexperienced laboratory user ("Inexperienced"), manager. Such roles enable a secure and efficient access control. The use of a laboratory instrument provided with the access control device is safe and efficient.

This prevents, in a simple manner, a user, for example due to lack of qualification, from performing certain operations on the laboratory instrument which could possibly lead to damage or inefficient use of the laboratory instrument or to increased costs during operation, e.g. due to excessive use of consumables used for a treatment.

The access control preferably provides at least one role, or more than one role, which can be assigned simultaneously to a user. Therefore, an individual can, for example, obtain access as administrator or as normal laboratory user, depending on a further condition. The user can preferably decide himself the role in which he obtains access to the laboratory instrument. However, it is also possible that the user does not decide this himself, but that this is decided by the access control device. This condition may be the data record used for authentication purposes, in particular the used password, or it may depend on a parameter of the laboratory instrument, in particular on an operating parameter of the laboratory instrument, e.g. an operating parameter which characterizes an error state of the laboratory instrument.

Preferably, the control apparatus of the access control device and/or the control apparatus of the laboratory instrument comprises a timer, in particular a clock, and/or, in particular, a booking apparatus, which comprises a storage apparatus which stores booking data, which, in particular, contain at least one booking data record or a plurality of booking data records, which describe at least one booking schedule, in particular individually for each treatment apparatus.

A booking data record contains, in particular, at least one of the items of information, in particular, which user, in particular at what time, carries out, has carried out or will carry out, in particular, which treatment of samples, in particular by means of which the laboratory instrument. The booking data preferably contain information about the bookings accepted by the booking apparatus, which bookings were in fact confirmed after comparison with the free capacities present in the booking schedule and were recorded in the booking schedule. However, the booking data may also contain booking requests, which the booking apparatus can recheck, in particular at a later time after the request was placed, and possibly accept at a later date, for example if an earlier entry in the reservation schedule was subsequently cancelled. The reservation data record preferably also contains information about what type of treatment is in each case planned on the laboratory instrument, what specific period of time or what duration of occupying the laboratory instrument is envisaged in the process and/or information about the process program used, and preferably contains, in particular, at least one program parameter or control parameter.

Preferably, the access control device is configured to transmit to a user upon request at least one item of information about the booking schedule, in particular to transmit the whole or part of the booking schedule or to transmit at least one change in the booking schedule. Preferably, the access control device is configured to transmit a notification automatically to a user, depending on at least one condition. This condition could be the change in the reservation schedule of a laboratory instrument, in particular in relation to the availability of a date for carrying out a treatment, in particular the release or cancelling of a date.

The "type of treatment" is, in particular, predetermined by the program parameters characterizing treatment. Such program parameters are, in particular, used by the control apparatus to generate a process program. In particular, a process program is a control code for controlling the treatment by means of control parameters. In particular, the control parameters are generated by the control apparatus, in particular by a control program running on the control apparatus, e.g. an operating system, while using the program parameters. The treatment of a sample is carried out, in particular, by virtue of a process program being executed by the control apparatus.

A "type of treatment" means a process, namely a type of application (e.g. "MagSep Blood gDNA", "Compose Mastermix" etc.). In a preferred configuration of the laboratory instrument as laboratory machine, the user initially selects a desired application, i.e. a "type of treatment", by virtue of selecting an application, in particular on the touchscreen of an instrument. This application, which is also referred to as "process", is, in particular, assigned to a program module which, in particular, may be a constituent of the control program. In particular, at least one program parameter is queried by the user by means of the program module. A program module generates, in particular, a process program on the basis of the at least one program parameter selected by the user.

Preferably, the control apparatus of the access control device and/or the control apparatus of the laboratory instrument is embodied to store booking data in the storage apparatus of the booking apparatus.

Preferably, the control apparatus of the access control device and/or the control apparatus of the laboratory instrument is configured to record the booking data record entered by the user into the laboratory instrument, in particular by means of the user interface apparatus or a portable or mobile user interface apparatus.

Preferably, the control apparatus of the access control device and/or the control apparatus of the laboratory instrument is embodied to compare the booking data record entered by the user with booking data already stored in the storage apparatus of the user interface apparatus.

Preferably, the control apparatus of the access control device and/or the control apparatus of the laboratory instrument is configured to store at least one, some or all booking data records, entered by at least one user, in the storage apparatus.

Preferably, the control apparatus of the access control device and/or the control apparatus of the laboratory instrument is embodied to evaluate some or all booking data records, entered by at least one user and stored in the storage apparatus, in accordance with an evaluation method stored in the storage apparatus and to create the schedule according to at least one criterion by virtue of the booking data records being sorted in accordance with the at least one criterion of a sort method stored in the control apparatus.

Preferably, the control apparatus of the access control device and/or the control apparatus of the laboratory instrument is embodied for the evaluation method to assign the at least one booking data record a priority, which priority is established in accordance with at least one criterion.

The criterion can, in particular, be represented by a data table stored in the control apparatus, in which data table e.g. the priority is related to at least one other parameter, wherein this other parameter may characterize e.g. the user or a user group, or the classification of a treatment in accordance to a list of relevance (e.g. from important to unimportant, expensive to cost-effective, etc.).

Preferably, the control apparatus of the access control device and/or the control apparatus of the laboratory instrument is embodied in such a way that the sort method sorts at least two booking data records in accordance with at least one criterion in order, in particular, to create a schedule which uses other time data than what is provided for in the booking data records of the users.

The criterion can be selected in accordance with the definitions in the evaluation method. Preferably, in order to realize a preferred criterion, the control apparatus is embodied to sort the booking data records under the aspect of a resource being optimized.

By way of example, the resource can be the time; in particular, a minimization of the waiting times can be sought after, a user in each case experiencing said waiting times as the difference between the start time, as desired by said user, and the start time, assigned by the laboratory instrument after evaluation and sort, for the experiment of said user, i.e. the treatment desired by said user. The minimization of the passive time, during which a laboratory instrument is not used, may also be sought after. In particular, it is also possible to plan intermediate servicing, cleaning and/or sterilization procedures, during which e.g. at least one workspace of at least one laboratory instrument or laboratory machine is prepared, in particular prepared manually and/or automatically, and/or cleaned and/or sterilized.

The resource may also be the energy which, as a function of the sequence of treatments, is possibly consumed to a different extent over different and successive ones of said treatments.

The resource may be a consumable, in particular a substance, e.g. a cleaner, or specific transport containers, e.g. pipette tips, or storage containers, e.g. microtiter plates, which, as a function of the sequence of treatments, are consumed to a different extent over various and successively carried out ones of said treatments. The same processes are possibly used in treatments planned by different users, and so it may be efficient to sort bookings on the basis of the processes. By way of example, it is conceivable that a specific substance and/or a specific consumable and/or a specific tool is used in a plurality of processes planned by different (or the same) users. Then, it may be particularly efficient to store this substance or this consumable or this tool in the laboratory instrument such that some transport processes become superfluous, as a result of which time and, optionally, the resource itself are saved, which resources often need to be stored under sterile conditions. By way of example, it would also be possible for two treatments, provided temporally in succession in the booking schedule, to be able to share specific consumables. By way of example, one and the same storage container could be used in both treatments, and therefore it is efficient to use the storage container for the second treatment after completion of the first treatment instead of disposing of the first storage container at the end of the first treatment and using a further storage container at the beginning of the second treatment. Moreover, it would for example also be possible to combine two separate bookings for an identical treatment and to work together in a single consumable (microtitre plate) in one treatment. As a result, it is possible to save material and time in many situations.

The resource can also be the plurality of laboratory instruments, on which the bookings occurring during a booking period of time are to be distributed automatically in accordance with the plurality of booking data records from a plurality of users in order to obtain an optimal use of the parks of laboratory instruments available in the laboratory. In particular, there may be experiments which require the synchronized use of more than one laboratory instrument. The resource may therefore consist of using a plurality of laboratory instruments optimally in time, in particular taking into account at least one experiment or a plurality of experiments which may each require different laboratory instruments.

The term "treatment" means, in particular, that a laboratory sample, which is usually in liquid form, is moved, transported and/or examined and/or modified, in particular modified physically, chemically, biochemically or in another way in terms of the composition thereof.

The term "instrument-controlled treatment" means that the treatment of the at least one laboratory sample is at least partly controlled, in particular performed, by the laboratory instrument. To the extent that the treatment is controlled and/or carried out by the laboratory instrument, said treatment in this respect is, in particular, not controlled and/or performed by the user, in particular not controlled and/or performed manually by the user.

An instrument-controlled treatment is furthermore preferably understood to mean that the treatment is at least partly controlled, in particular performed, by the laboratory instrument as a function of at least one user input. The user input may occur prior to the start of the treatment and/or during the treatment. The user input preferably occurs using a user interface apparatus, which is preferably a component of the laboratory instrument or which is provided separately from the laboratory instrument and signal connected to the control apparatus of the laboratory instrument and/or to the control apparatus of the access control device. The user input serves, in particular, for entering at least one parameter, the value of which influences and/or controls the treatment. This paramter can, in particular, be a program parameter.

The "instrument-controlled treatment" denotes, in particular, the at least partly automated treatment. In the case of the partly automated treatment, it is possible, in particular, for the treatment to be performed in such a way that, after the treatment has started and before the treatment is complete, there is at least one user input, by means of which the user can influence current treatment, in particular by virtue of said user e.g. responding to an automatic query brought about by means of a user interface apparatus of the laboratory instrument, in particular by virtue of confirming or denying an input or undertaking other inputs. In the case of the partly automated treatment, it is possible, in particular, for the treatment to have a plurality of treatment steps which, in particular, are performed automatically and successively in time and which have at least one treatment step that requires a user input, which, in particular, is brought about via a user interface apparatus.

An instrument-controlled treatment is preferably a program-controlled treatment, i.e. a treatment controlled by a program. A program-controlled treatment of a sample should be understood to mean that the process of treatment substantially takes place by working through a plurality or multiplicity of program steps. Preferably, the program-controlled treatment takes place using at least one program parameter, in particular at least one program parameter selected by the user. A parameter selected by a user is also referred to as a user parameter. The program-controlled treatment preferably takes place with the aid of a digital data processing apparatus which, in particular, may be a component of the control apparatus of the laboratory instrument. The data processing apparatus can comprise at least one processor, i.e. a CPU, and/or at least one microprocessor. The program-controlled treatment is preferably controlled and/or performed in accordance with the prescriptions of a program, in particular a control program. In particular, substantially no user activity is required in the case of a program-controlled treatment, at least after acquisition of the program parameters required from the user.

A program parameter is understood to mean a variable which can be set in a predetermined manner within a program or sub-program and is valid for at least one execution (call) of the program or sub-program. The program parameter is set, e.g. by the user, and controls the program or sub-program and causes a data output as a function of this program parameter. In particular, the program parameter influences and/or controls the control of the instrument, and/or the data output by the program control said instrument, in particular the control of the treatment by means of the at least one treatment apparatus.

A program parameter may be a program parameter required on the part of the user. A program parameter required on the part of the user is distinguished by the fact that it is required for performing a treatment, in particular for performing a process program. Other program parameters, which are not required on the part of the user, may be derived from the program parameters required on the part of the user or may be made available in a different manner, in particular they may optionally be set by the user. In particular, a program parameter is set by a user by displaying a selection of possible predetermined values from a list of predetermined values stored in the laboratory instrument, wherein the user selects, and therefore sets, the desired parameter from this list. It is also possible for this program parameter to be set by virtue of the user entering the value, e.g. by virtue of entering a numeric number corresponding to the desired value by means of a numeric pad or by virtue of said user increasing or reducing a value continuously or in increments until said value corresponds to the desired value and the value is set thus.

A program is, in particular, understood to mean a computer program. A program is a sequence of statements, in particular consisting of declarations and instructions, enabling a specific functionality, object or problem to be handled and/or solved on a digital data processing system. A program is generally available as software which is used with a digital data processing system. In particular, the program can be available as firmware, in particular as firmware of the control apparatus of the laboratory instrument and/or of the access control device in the case of the present invention. The program is usually available as a program file, often in the form of so-called machine code, which can be executed on a data medium, which program file is loaded into the main memory of the computer of the digital data processing system for execution purposes. The program is processed and therefore executed by the processor(s) of the computer as a sequence of machine commands, i.e. processor commands. In particular, a "computer program" is also understood to mean the source text of the program from which the executable code can be generated from the progress of the control of the laboratory instrument.

As is conventional, a statement denotes a central element of a programming language. Programs of such languages are primarily composed of one or more statements. A statement constitutes a single prescription, formulated within the syntax of a programming language, which prescription is to be executed when working through the program. The syntax of a statement is set by the respective programming language or the specification thereof. In machine-oriented programming, statements are often also referred to as commands.

Statements are usually assignments, control statements (such as branches, loops and conditional statements) and procedural calls. Depending on the programming language, assertions, declarations, class definitions and function definitions are also in part statements. Thus, the statements of the control program can be configured in a conventional manner.

As is conventional, a program module is understood to be a complete functional unit of software, consisting of a sequence of processing steps and data structures. Here, in particular, the following definitions may apply: the content of a module is often a recurring calculation or handling of data, which needs to be carried out a number of times. Modules offer an encapsulation by separating interface and implementation: the interface of a module defines the data elements which, as input and result of the processing, are required by the module. The implementation contains the actual program code. By way of example, a module is called as a function or sub-program, executes a number of processing steps and, as a result, provides data back to the calling program. A module itself is able to call further modules—thus, a hierarchy of program calls is possible. The data structures and processes set in modules can, when necessary, be inherited and inherited by other modules. Therefore, modules are an essential element in structured and object-oriented programming.

A control program is understood to mean an executable computer program, which preferably controls and/or performs the desired treatment of the at least one sample, in particular as a function of at least one program parameter. This program parameter can be a program parameter influenced and/or set by the user. In particular, the treatment can be controlled by virtue of the control apparatus generating one or more control parameters as a function of the program parameters, by means of which control parameters the at least one treatment apparatus is controlled. The laboratory instrument preferably has an operating system, which can be or comprise a control program. In particular, the control program can denote an operating system of the laboratory instrument or a component of the operating system. The operating system controls the treatment and further operating functions of the laboratory instrument In particular, the control program can be signal connected to the access control device and/or can control the access control device. The control apparatus of the access control device can be integrated into the control apparatus of the laboratory instrument or can be embodied separately from this control apparatus. The access control device can be integrated into the control apparatus of the laboratory instrument. The control device of the access control device can be integrated into control device of the laboratory instrument, can be controllable by the control program and/or can, in particular, be integrated into the control program. The control program can control further preferably provided functions of the laboratory instrument, for example an energy-saving function of the laboratory instrument or a communication function for communication with external data processing apparatuses which, in particular, are provided separately from the laboratory instrument and, in particular, are not a component of the laboratory instrument.

A process program is understood to mean a program which determines the specific progress of a treatment, in particular in accordance with a predetermined type of treatment and/or in accordance with a manner set on the part of the user.

The invention furthermore relates to a laboratory instrument for instrument-controlled treatment of at least one laboratory sample, which laboratory instrument comprises at least one treatment apparatus for performing the treatment of the at least one laboratory sample, and an access control device according to the invention.

Preferably, the laboratory instrument comprises a communication apparatus for establishing a remote data connection for data interchange with an external instrument, which likewise comprises a suitable communication apparatus for establishing a remote connection for data interchange with the laboratory instrument. Such a communication apparatus can be embodied for establishing a radio connection, in particular a mobile communications connection. The communication apparatus is preferably configured to enable remote access of the user to the laboratory instrument, in particular for selecting or setting of at least one parameter, in particular a parameter which controls a function of the laboratory instrument, in particular the function of performing a treatment.

Preferably, the control apparatus of the access control device or of the laboratory instrument is embodied to provide synchronization data. Preferably, the access control device, in particular the control apparatus of the access control device, is configured in such a way that, if at least one condition is satisfied, information about the operating state of the laboratory instrument, measured values or settings and programs of the laboratory instrument which can be influenced by the user are transmitted to the second user interface apparatus via the interface apparatus. As a result of this information transfer, the laboratory instrument, in particular a treatment running thereon, can continue to be observed and/or controlled by means of the second user interface apparatus. In particular, the use state of the first interface apparatus can be partly or completely copied or cloned in the second user interface apparatus. The information transfer can, in particular, be a synchronization process. The first and second user interface can be synchronized, in particular in this manner. The at least one other condition may be that the access of the accessing user is brought about by means of a remote data connection via a (mobile) user interface apparatus and the request of the user is brought about after synchronization. The at least one other condition can moreover be the condition a) or b), namely the response to the check whether the logging-on user has already previously, via a first user interface apparatus, a) activated one or more currently executed functions of the laboratory instrument or b) logged on. In cases a) and b), the synchronization would only be allowed for a user with an active session and/or with currently activated functions on the laboratory instrument, in particular with running treatments which were initiated by the user. However, it is also possible and preferred for a further user to be allowed to carry out synchronization, e.g. in order to perform remote control for the purpose of providing assistance during the current session or treatment or for the purpose of carrying out servicing works, etc.

Preferably, the control apparatus of the access control device is configured to transfer these synchronization data to an—in particular mobile—user interface apparatus. Preferably, these synchronization data are suitable for displaying the information displayed in the display of the user interface apparatus at least partly in an identical manner on the display of the—in particular mobile—user interface apparatus.

The term laboratory instrument denotes, in particular, an instrument which is embodied for instrument-controlled treatment of at least one laboratory sample and which is embodied for use in a laboratory. This laboratory can be, in particular, a chemical, biological, biochemical, medical or forensic laboratory. Such laboratories serve for research and/or analysing laboratory samples, but can also serve for the manufacture of products by means of laboratory samples or the manufacture of laboratory samples.

A laboratory instrument is preferably one of the following laboratory instruments and/or is preferably embodied as at least one of the following laboratory instruments: a laboratory centrifuge, also referred to as "centrifuge" within the scope of the description of the present invention; a thermocycler, also referred to as "cycler" within the scope of the description of the present invention; a laboratory spectral photometer, also referred to as "biospectrometer" within the scope of the description of the present invention; a cell counting instrument, also referred to as "cell counter" within the scope of the description of the present invention, in particular optical counting instruments; a laboratory incubator, also referred to as "incubator" within the scope of the description of the present invention; a laboratory shaker, also referred to as "shaker" within the scope of the description of the present invention; a laboratory mixer, also referred to as "mixing device"; a laboratory freezer, also referred to as "freezer" within the scope of the description of the present invention; a bioreactor, also referred to as fermenter within the scope of the description of the present invention; a safety work bench, in particular biological safety cabinet, also referred to as "biosafety cabinet" within the scope of the description of the present invention; a sample plate reader, also referred to as "plate reader" within the scope of the description of the present invention, in particular "microplate reader"; a laboratory machine for treating fluid samples, in particular a pipetting machine.

A laboratory centrifuge is an instrument which works using inertia. The laboratory centrifuge, in particular the treatment apparatus of the laboratory centrifuge, comprises, in particular, at least one rotor, in which the at least one laboratory sample can be disposed. The at least one rotor is disposed rotatably in at least one centrifuge vessel. The laboratory centrifuge, in particular the treatment apparatus of the laboratory centrifuge, comprises at least one drive apparatus, by means of which the rotation is driven and/or braked. The samples can be disposed in the at least one rotor, preferably in laboratory containers, e.g. sample tubules, which are disposed in suitable holders in the rotor. The laboratory centrifuge, in particular the treatment apparatus of the laboratory centrifuge, preferably comprises at least one heater/cooling apparatus, by means of which the temperature of the at least one sample disposed in the rotor can be controlled and/or regulated. The laboratory centrifuge, in particular the treatment apparatus of the laboratory centrifuge, preferably comprises a timer apparatus, by means of which time parameters of the rotation or temperature settings can be controlled. The functionality is based upon the centrifugal force, which occurs due to a uniform circular motion of the samples to be centrifuged. The centrifugal force is used for substance separation of substances with different densities, which are contained in a sample. A centrifuge can perform a separation method, in which, in particular, the constituents of suspensions, emulsions and/or gas mixtures are separated. The instrument-controlled treatment of the at least one laboratory sample corresponds to a rotational treatment in a laboratory centrifuge, with at least one sample being subjected to said rotational treatment. Possible parameters, in particular program parameters, in particular user parameters, which are used to influence a rotational treatment, define, in particular, a temperature of the laboratory centrifuge, a rotational speed of the laboratory centrifuge, a time parameter of the rotation or a temperature setting and/or at least one progress parameter, which influences or defines the progress, in particular the sequence, of a rotation program consisting of a plurality of rotation steps. The temperature of the laboratory centrifuge can, in particular, be at least one temperature in the interior of the at least one rotor, in particular at least one temperature of at least one sample.

A thermocycler is an instrument that is able, successively in time, to set the temperature of at least one sample to a predetermined temperature and to keep said sample at this temperature level for a predetermined duration. The progress of this temperature control is cyclical. That is to say, a predetermined temperature cycle, i.e. a sequence of at least two temperature levels, is carried out repeatedly. This method serves, in particular, for performing a polymerase chain reaction (PCR). In this context, a thermocycler is sometimes also referred to as a PCR block. A thermocycler, in particular the treatment apparatus of the thermocycler, preferably has a thermoblock. A thermoblock is a sample holder made of a heat-conducting material, usually a metal-containing material or a metal, in particular aluminium or silver. The sample holder comprises a contacting side which is contacted by at least one heater/cooling apparatus of the thermocycler, in particular by a Peltier element. The thermocycler, in particular the treatment apparatus of the thermocycler, comprises a regulation apparatus with at least one control loop, to which the at least one heater/cooling apparatus is assigned as an actuator and at least one temperature measurement apparatus is assigned as a measurement member. The temperature is regulated to a temperature level by means of the controlling system. A cooling body of the thermocycler, in particular of the treatment apparatus of the thermocycler, serves for cooling sections of the thermocycler, in particular for cooling the Peltier elements. The thermocycler, in particular the treatment apparatus of the thermocycler, may comprise further heater and/or cooling elements. The thermocycler, in particular the treatment apparatus of the thermocycler, preferably comprises a timer apparatus, by means of which time parameters for setting the temperature cycle can be controlled. The instrument-controlled treatment of the at least one laboratory sample corresponds to a temperature cycle treatment in a thermocycler, with at least one sample being subjected to said rotational treatment. Possible parameters, in particular program parameters, in particular user parameters, which are used to influence a temperature cycle treatment, define, in particular, the temperature of the temperature level, the duration of a temperature level, the control of further heater and/or cooling elements and/or the number of temperature levels or cycles and/or at least one progress parameter, which influences or defines the progress, in particular the sequence, of a temperature monitoring program consisting of a plurality of steps.

A laboratory spectrophotometer is an instrument which, by illuminating at least one measurement volume of at least one laboratory sample, usually over the whole spectrum of visible light from infrared to ultraviolet, establishes the values of diffuse reflection. Diffuse reflection refers to the situation in which a measurement volume absorbs part of the light spectrum and transmits part of the spectrum (transparent media) or reflects it (opaque media). The laboratory spectrophotometer is used, in particular, to measure the absorptivity of a sample as a function of the light wavelength. Moreover, it is possible, in particular, to extend the field of application of the laboratory spectrophotometer by means of various modules. By way of example, it is conceivable to dispose a fluorescence module for measuring fluorescence or a temperature-control module for controlling the temperature of the sample in the spectrometer. The measured absorption spectrum contains, in particular, the light intensities measured at specific wavelengths. The absorption spectrum is typical of the laboratory sample or the substance contained therein or the substances. This can be used for qualitative analysis of the laboratory sample. If the liquid sample or the substance dissolved therein is known, the concentration of the dissolved substance can be established by measuring the absorption. This can be used for quantitative analysis of the laboratory sample. The laboratory spectrophotometer, in particular the treatment apparatus of the laboratory spectrophotometer, preferably comprises at least one light source, preferably at least one timer, preferably at least one photodetector. The instrument-controlled treatment of the at least one laboratory sample corresponds to a light and measurement treatment in a laboratory spectrophotometer, with at least one sample being subjected to said treatment. Possible parameters, in particular program parameters, in particular user parameters, which are used to influence a light and measurement treatment, define, in particular, the optical light spectrum, by means of which the at least one sample is irradiated and/or at least one progress parameter, which influences or defines the progress, in particular the sequence, of a light and measurement treatment program consisting of a plurality of steps.

A cell counting instrument serves for counting biological cells or particles which are contained in the laboratory sample. There are different physical principles which can be used to count cells, in particular optical methods, in which the laboratory sample to be measured is disposed in a counting chamber and illuminated, and an image of the cells or particles disposed in the counting chamber is acquired and evaluated. A cell counting instrument embodied as a Coulter counter guides the laboratory sample containing the cells through a measurement port. Each passage of a cell through the measurement port is detected electrically as a countable event. The cell counting instrument, in particular the treatment apparatus of the cell counting instrument, preferably comprises, depending on the embodiment, at least one light source, at least one image acquisition unit and at least one image evaluation unit, or a chamber apparatus with measurement port, a pump apparatus and an electrical measurement apparatus. In the case of a cell counting instrument, the instrument-controlled treatment of the at least one laboratory sample corresponds e.g. to a light and measurement treatment or a pumping and measurement treatment, to which treatment the at least one sample is subjected. Possible parameters, in particular program parameters, in particular user parameters, which are used to influence a light and measurement treatment or the pumping and measurement treatment, define, in particular, the light intensity of the light source, by means of which the at least one sample is irradiated and/or at least one progress parameter, which, which influences or defines the progress, in particular the sequence, of a light and measurement treatment or the pumping and measurement treatment program consisting of a plurality of steps.

A cell counting instrument serves for counting biological cells or particles which are contained in the laboratory sample. There are different physical principles which can be used to count cells, in particular optical methods, in which the laboratory sample to be measured is disposed in a counting chamber, there is additional illumination, particularly in the case of automatically operating ones, and an image of the cells or particles disposed in the counting chamber is acquired and evaluated. A further established method lies in measuring the impedance: a cell counting instrument embodied as a Coulter counter guides the laboratory sample containing the cells through an aperture ("measurement port"). Each passage of a cell through the aperture is detected electrically as a countable event. Optical cell counting instruments, in particular the treatment apparatus of the cell counting instrument, preferably comprise, depending on the embodiment, at least one light source, at least one image acquisition unit and at least one image evaluation unit, and additionally, inter alia, a positioning apparatus. The instrument-controlled treatment of the at least one laboratory sample corresponds e.g. to a light and measurement treatment in the case of an optical cell counting instrument, a pumping and measurement treatment in the case of an instrument operating according to the Coulter principle, to which treatment the at least one sample is subjected. Possible parameters, in particular program parameters, in particular user parameters, which are used to influence a light and measurement treatment or the pumping and measurement treatment, define, in particular, the light intensity of the light source, by means of which the at least one sample is irradiated and/or at least one progress parameter, which influences or defines the progress, in particular the sequence, of a light and measurement treatment program or a pumping and measurement treatment program consisting of a plurality of steps. Moreover, in the case of optical counting instruments, the algorithms necessary for the image evaluation, and the sequence and parameterization thereof are decisive for the significance of the measurement result. Optical measurement instruments, but also Coulter counters, often use counting chambers for single use ("consumables"); these are plastic articles in the style of conventional Neubauer counting chambers or, in the case of Coulter counters, "lab-on-a-chip"-like disposable counting chambers. However, there are also instruments which operate without these consumables (e.g. "CASY").

A laboratory incubator is an instrument by means of which controlled climatic conditions for various biological development and growth processes can be set up and maintained. It serves to set up and maintain a microclimate with regulated gas and/or humidity and/or temperature conditions in an incubator space, wherein this treatment may be dependent on time. The laboratory incubator, in particular the treatment apparatus of the laboratory incubator, comprises, in particular, a timer, in particular a timer switch, a heater/cooling apparatus and preferably a setting for regulating the substitute gas supplied to the incubator space, in particular fresh air, a setting apparatus for the composition of the gas in the incubator space of the laboratory incubator, in particular for setting the $CO_2$ and/or $O_2$ content of the gas and/or a setting apparatus for setting the humidity in the incubator space of the laboratory incubator. The laboratory incubator, in particular the treatment apparatus of the laboratory incubator, comprises, in particular, the incubator space, furthermore preferably a regulation apparatus with at least one control loop, to which at least one heater/cooling apparatus is assigned as an actuator and at least one temperature measurement apparatus is assigned as a measurement member. The temperature can be regulated in the incubator by means of the controlling system. $CO_2$ incubators serve, in particular, for cultivating animal or human cells. Incubators may have turning devices for turning the at least one laboratory sample and/or a shaker apparatus for shaking or moving the at least one laboratory sample. The instrument-controlled treatment of the at least one laboratory sample corresponds to a climate treatment in a laboratory incubator, with at least one sample being subjected to said treatment. Possible parameters, in particular program parameters, in particular user parameters, which are used to influence a climate treatment, define, in particular, the temperature of the incubator space, in which the at least one sample is incubated, the $O_2$ and/or $CO_2$ partial pressure in the incubator interior, the humidity in the incubator interior and/or at least one progress parameter, which influences or defines the progress, in particular the sequence, of a incubation treatment program consisting of a plurality of steps.

A laboratory shaker serves for moving a laboratory sample, in particular for mixing a laboratory sample comprising a plurality of constituents. There are different embodiments of laboratory shakers, in particular overhead shakers or flatbed shakers. Laboratory shakers can comprise a temperature control function for controlling the temperature of at least one laboratory sample and can, in particular, comprise an incubator function for incubating the at least one laboratory sample in controlled climatic conditions. Laboratory shakers, in particular the treatment apparatus thereof, can, in particular, be configured to perform an oscillating motion. Laboratory shakers, in particular the treatment apparatus thereof, comprise, in particular, a drive for driving the motion, comprise, in particular, a timer apparatus, by means of which time parameters of the setting of the shaker treatment can be controlled and, in particular, comprise at least one heater/cooling apparatus and at least one control apparatus with at least one control loop, which is assigned the at least one heater/cooling apparatus as actuator and at least one temperature measurement apparatus as measurement member. The instrument-controlled treatment of the at least one laboratory sample corresponds to a shaker treatment in a laboratory shaker, with at least one sample being subjected to said treatment. Possible parameters, in particular program parameters, in particular user parameters, which are used to influence a shaker treatment, define, in particular, the movement intensity, in particular the movement frequency in the case of an oscillating drive, a time period during the shaker treatment and/or at least one progress parameter, which influences or defines the progress, in particular the sequence, of a shaker treatment program consisting of a plurality of steps.

A laboratory mixer, also referred to as "mixing device", serves like the laboratory shaker for moving a laboratory sample, in particular for mixing a laboratory sample comprising a plurality of constituents. Compared to a laboratory shaker, a laboratory mixer enables movements with higher frequencies, in particular with higher rotational speeds. Laboratory mixers, in particular the treatment apparatus thereof, can, in particular, be configured to perform an oscillating motion. Laboratory mixers, in particular the treatment apparatus thereof, comprise, in particular, a drive for driving the motion, comprise, in particular, a timer apparatus, by means of which time parameters of the setting of the mixer treatment can be controlled and, in particular, comprise at least one heater/cooling apparatus and at least one control apparatus with at least one control loop, which is assigned the at least one heater/cooling apparatus as actuator and at least one temperature measurement apparatus as measurement member. The instrument-controlled treatment of the at least one laboratory sample corresponds to a mixer treatment in a laboratory mixer, with at least one sample being subjected to said treatment. Possible parameters, in particular program parameters, in particular user parameters, which are used to influence a mixer treatment, define, in particular, the movement intensity, in particular the movement frequency in the case of an oscillating drive, a time period during the mixer treatment and/or at least one progress parameter, which influences or defines the progress, in particular the sequence, of a mixer treatment program consisting of a plurality of steps.

A laboratory freezer serves for storing at least one laboratory sample in a freezer room at regulated temperatures, in particular in the freezer range from −18° C. to −50° C. or in the ultra-freezer range from −50° C. to −90° C. In particular, a laboratory freezer is not a refrigerator, which can be used for cooling at temperatures in the range from 0° C. to 10° C. or from −10° to 10° C. in particular. A laboratory freezer, in particular the treatment apparatus of the laboratory freezer, comprises, in particular, at least one cooling apparatus and at least one regulation apparatus with at least one control loop, to which at least one cooling apparatus is assigned as an actuator and at least one temperature measurement apparatus is assigned as a measurement member. A laboratory freezer, in particular the treatment apparatus of the laboratory freezer, comprises, in particular, a monitoring measurement instrument for measuring the temperature and/or in particular at least one alarm apparatus, by means of which an alarm signal is emitted if the temperature measured in the freezer space departs from a permitted temperature range. A laboratory freezer, in particular the treatment apparatus of the laboratory freezer, can, in particular, comprise an information reader for reading information. This information can be contained in an information medium which can be connected to an article. This article can, in particular, be a sample container, in particular a storage container, which can contain at least one laboratory sample. The information medium can, in particular, comprise an RFID chip or other identification features, such as e.g. a barcode, a data matrix code, a QR code, which can be read by suitable methods. The instrument-controlled treatment of the at least one laboratory sample corresponds to a low-temperature treatment in a laboratory freezer, with at least one sample being subjected to said treatment. Possible parameters, in particular program parameters, in particular user parameters, which are used to influence a low-temperature treatment, define, in particular, the temperature of the freezer space, in which the at least one sample is frozen and/or the information read process, which is preferably carried out when an article provided with an information medium is transferred from a user into the laboratory freezer. It is also possible and preferred for the laboratory instrument according to the invention not to be a laboratory freezer.

A bioreactor comprises a container, in which specific microorganisms, cells, *algae*, plants, e.g. mosses, are cultivated (also: fermented) under conditions which are as ideal as possible. The operation of a bioreactor therefore is an application of biotechnology, which, in technical apparatuses, uses biological processes, in particular bioconversion or biocatalysis, or makes these available. Factors which can be controlled or monitored in most bioreactors, in particular by setting appropriate parameters, are the composition of the nutrient solution, the oxygen supply, temperature, pH, sterility and/or other factors. The purpose of cultivation in a bioreactor may be the harvesting of cells or constituents of cells, or the harvesting of metabolic products. By way of example, these can be used as an active ingredient in the pharmaceutical industry or as a basic chemical in the chemical industry. The breakdown of chemical compounds may also take place in bioreactors, such as e.g. in sewage water treatment in sewage works. The production of beer, wine and other such products likewise occurs in bioreactors. The most diverse type of organisms are cultivated in bioreactors for various purposes. A bioreactor can therefore have different configurations. It can be configured as stirred tank reactor made of metal, which can have a volume from a few millilitres to hundreds of litres and can be filled with nutrient solution. It can also be used or embodied as a fixed bed reactor or photobioreactor. In particular, a bioreactor can also be embodied as single-use bioreactor, in which the reactor container, in particular including the stirrer, consists of plastic, for example the Celligen® BLU single-use bioreactor from Eppendorf AG. A bioreactor can be part of a bioreactor system, preferably of a parallel bioreactor system. In such a parallel bioreactor system, a multiplicity of bioreactors are operated in parallel and controlled with high precision. A bioreactor, in particular the treatment apparatus thereof, comprises, in particular, a stirring apparatus for stirring the sample contained in the reactor container, in particular for stirring the nutrient solution. A bioreactor, in particular the treatment apparatus thereof, comprises, in particular, a pump apparatus for pumping the laboratory sample, which is preferably configured as nutrient solution. A bioreactor, in particular the treatment apparatus thereof, comprises, in particular, a setting apparatus for setting a gas content in the reactor container, in particular the content of $CO_2$ and/or $O_2$ or of dissolved oxygen (DO). A bioreactor, in particular the treatment apparatus thereof, comprises, in particular, a setting apparatus for setting, in particular regulating, a pH value in the sample in the reactor container. The instrument-controlled treatment of the at least one laboratory sample corresponds to, in particular, a nutrient solution treatment in a bioreactor, with at least one sample, preferably embodied as nutrient solution, being subjected to said treatment. Possible parameters, in particular program parameters, in particular user parameters, which are used to influence a nutrient solution treatment, define, in particular, the temperature of the nutrient solution in the reactor container and/or the speed of the stirrer apparatus, in particular the rotational speed and/or the pump speed or the metering speed and/or a gas content in the nutrient solution, in particular $CO_2$ and/or $O_2$ or dissolved oxygen (DO) and/or the pH value of the nutrient solution and/or at least one progress parameter, which influences or defines the progress, in particular the sequence, of a nutrient solution treatment program consisting of a plurality of steps.

A biological safety cabinet serves, in particular, for secure storage or stockpiling of hazardous materials, in particular for meeting a biological protection level. In particular, these levels are standardized in EU Directive 2000/54/EG on the protection of workers from risks related to exposure to biological agents at work and, in Germany, in the German Ordinance on Biological Substances. A biological safety cabinet is intended to prevent laboratory samples stored in a biological safety cabinet from endangering the surroundings if danger develops. In particular, safety is ensured by virtue of the atmosphere contained in the receiving region of the biological safety cabinet being replaced and, in particular, filtered. Here, in particular, this atmosphere is conveyed through the receiving region by a conveying apparatus and moved through a filter, which filters the atmosphere and, in particular, removes hazardous materials. The biological safety cabinet, in particular the treatment apparatus thereof, comprises, in particular, a conveying apparatus for conveying atmospheric gas, comprises, in particular, a timer apparatus for measuring a filter operation duration and a ventilator operation duration and/or comprises, in particular, a measurement apparatus for measuring a conveyed amount of atmospheric gas. The instrument-controlled treatment of the at least one laboratory sample corresponds, in particular, to an atmospheric gas treatment for treating the atmospheric gas, in which the at least one sample is stored, in a biological safety cabinet. Possible parameters, in particular program parameters, in particular user parameters, which are used to influence an atmospheric gas treatment, define, in particular, the temperature of the atmospheric gas in the receiving region and/or the flow speed of the atmospheric gas conveyed by the conveying apparatus, the amount of air conveyed, the filter operation duration and/or the ventilator operation duration.

A sample plate reader, also referred to as "plate reader" or "microplate reader", is a laboratory instrument for detecting biological, chemical or physical events of samples in microtitre plates. They are used widely in research: for active ingredient research, bioassay validation, quality control and manufacturing processes in the pharmaceutical and biotech industry and in academic organizations. The sample plate reader can, in particular, comprise at least one light source or radiation source, can comprise at least one photodetector, can comprise a temperature control apparatus for the temperature control of the samples or the sample plates and can comprise a timer. Sample reactions can be tested in 6-1536 well microtiter plates. The most common format for sample plates, in particular microtiter plates, which are used in academic research laboratories or in clinical-diagnostic laboratories, is a 96 well plate (an 8 by 12 matrix) with a typical individual volume of between 100 and 200 µl per well. microtiter plates with a higher density (384 or 1536 well microtiter plates) are typically used in screening applications if the throughput (number of samples to be processed per day) and assay costs per sample become critical parameters, and these have a typical assay volume of between 5 and 50 µl per well. The treatment is, in particular, an optical measurement of the microtiter plate, in particular the measurement of an absorption, fluorescence intensity, luminescence, time-resolved fluorescence and/or fluorescence polarization. Possible parameters, in particular program parameters, in particular user parameters, which are used to influence a measurement, define, for example, the intensity of the light source, the sensitivity of the photodetector, a time duration and/or a temperature.

A laboratory machine for treating fluid samples, in particular an automatic pipette, serves for the program-controlled treatment of these samples. A laboratory machine can be a laboratory instrument or comprise at least one laboratory instrument of the aforementioned type and/or can be embodied to carry out at least one, some or all of the treatments that can be executed by this aforementioned laboratory instrument. A laboratory machine comprises the treatment apparatus for automatic, program-controlled treatment of the at least one laboratory sample, wherein the treatment is controlled by using a plurality of program parameters, which are at least partly selected by the user. In the process, the sample can, for example, be moved and/or transported by the laboratory machine or a treatment apparatus of the laboratory machine. The movement can be brought about by transport in movable sample containers or by guidance through tube systems, capillaries or pipette tips. Here, liquid samples are, in particular, transported by suction, i.e. by pipetting, or, more generally, by the application of pressure differences. By way of example, a sample can be divided or diluted by a treatment of the sample. The contents of a sample can be analysed or it is possible, e.g. by way of a chemical reaction, for new contents to be produced, in particular by using the sample. In the context of, in particular, handling and analysing DNA or RNA or the constituents thereof, laboratory machines aid in obtaining a wealth of information within a suitable period of time or in analysing many such samples. This treatment apparatus of a laboratory machine usually comprises a worktop with workstations, on which samples can be handled or stored in various ways. For the purposes of transporting e.g. liquid samples between various positions, in particular sample containers, the treatment apparatus usually comprises an instrument-controlled movement device and an instrument-controlled fluid-transfer apparatus, which can e.g. comprise a pipetting system. Both the transport of the samples and the treatment thereof at the various stations can be carried out in an instrument-controlled manner, in particular in a program-controlled manner. Then the treatment is preferably at least partly or completely automated.

The user of the laboratory machine can preferably set the type of treatment for the sample. Such a treatment type may, in particular, serve for:
nucleic acid purification, in particular:
"MagSep Blood gDNA": purification of genomic DNA from whole blood, in particular using the Eppendorf MagSep Blood gDNA kit;
"MagSep Tissue gDNA": purification of genomic DNA from living tissue, in particular using the Eppendorf® MagSep Tissue gDNA kit;
"MagSep Viral DANN/RNA": purification of viral RNA or DNA from cell-free bodily fluids, in particular using the Eppendorf® MagSep Viral DNA/RNA kit;
and PCR applications, in particular:
"Compose Mastermix";
"Normalize Concentrations";
"Create Dilution Series";
"Setup Reactions".

A laboratory instrument, in particular the laboratory machine, is preferably embodied in such a way that the treatment of the at least one laboratory sample can be controlled automatically using the acquired program parameters. The laboratory instrument, in particular the laboratory machine, in particular the control program thereof, is preferably embodied in such a way that the input undertaken by the user, in particular the at least one value of at least one program parameter, can be used, where necessary, to automatically establish further, required program parameters, in particular by calculation or comparison with data in a database of the laboratory instrument. In particular, the control parameters preferably used for performing the treatment in detail are preferably determined automatically. As a result of these measures, the operation of the laboratory instrument becomes more convenient, the user is spared from, in particular, designing a program code since these steps are carried out, in particular automatically, by the laboratory instrument, in particular the laboratory machine. In a preferred embodiment, all that is required from the user are the entries which are directly related to the treatment of the samples to be performed. Often, these are the same specifications that would also be necessary for performing the treatment manually and these are known to the user. By contrast, the parameters which relate to the control of the laboratory instrument, in particular of the laboratory machine, in particular the control parameters, need not be set in detail since these are preferably set automatically. Control parameters are the parameters required in detail for controlling the technical constituents of the treatment apparatus. Control parameters can be program parameters or can be parameters derived therefrom for the technical implementation, in particular automatically determined parameters.

Preferably, a laboratory instrument, in particular the laboratory machine, automatically selects the fitting set of program parameters following the treatment type selection by the user, wherein the program parameters thereof required on part of the user are then queried from the user in steps (b) and (c). The set of program parameters can contain, firstly, the program parameters required on part of the user and can contain, secondly, further program parameters. These further program parameters can be set automatically depending on the selected treatment of type or can be set automatically depending on at least one or all program parameters entered by the user and/or can be stored in the storage apparatus. The stored parameter sets are preferably optimized for the type of treatment—or become optimized by the laboratory instrument, in particular the laboratory machine—such as that the user preferably requires no specialist knowledge for optimizing the parameters. The control parameters which are necessary for performing the specific treatment by means of the treatment apparatus are derived from the program parameter set.

A program parameter set of program parameters specific to a treatment type is preferably defined for this treatment type. The program parameters of this program parameters set can, in particular, define the accessories to be used for the treatment, e.g. sample container, transport container and/or the further consumables and/or tools to be used.

The mapping between program parameter set and treatment type is stored in the storage apparatus of the laboratory instrument, in particular of the laboratory machine. Preferably, a laboratory instrument, in particular the laboratory machine, is embodied in such a way that the user can store and/or use more such mappings in a laboratory instrument, in particular the laboratory machine. The operation of the laboratory instrument becomes particularly efficient by these mappings in combination with the clear and well-structured querying of the program parameters. This mapping is preferably brought about by using one or more program modules, wherein a program module is respectively tailored to a specific application:

The treatment of a laboratory sample or samples can contain one or more of the processes specified below, in particular simultaneously or in succession:

transport of the laboratory sample, in particular by a transport apparatus, under the action of gravity and/or a force caused by the laboratory instrument, in particular the laboratory machine;

a contactless (non-invasive) physical treatment of the sample, in particular a thermal treatment, in particular heating and/or cooling, in particular controlling the temperature of the sample; or freezing or defrosting of the sample or a different thermal induction of a phase change of the sample, e.g. evaporation, condensation, etc.; a magnetic treatment of the sample; and optical treatment of the sample, in particular irradiating the sample with radiation, in particular light, in particular visible light, infrared light or UV light or detection of such radiation, in particular fluorescence light, from the sample; a magnetic treatment of the sample with magnetic constituents, in particular magnetic separation of magnetic constituents, in particular "magnetic beads", from a liquid phase of the sample; moving the sample, i.e. performing a mechanical treatment of the sample, in particular stirring, rotating, isolating, vibrating, centrifuging, an acoustic treatment, in particular with ultrasound, in each case e.g. for the purpose of mixing the sample or of separating constituents within the sample or of transporting the magnetic constituents out of the sample or into the sample;

invasive physical treatment of the sample, i.e. performing a mechanical treatment of the sample: introducing stirring tools, e.g. stirring bar or magnetic stirrer bar, into the sample and stirring, introducing a probe for acoustic or ultrasonic treatment, introducing transport means, in particular transport containers, into the sample, e.g. dispenser tip or pipette tip or hollow needle or tube; adding other auxiliary means into the sample;

chemical, biochemical or biomedical treatment of the sample: adding chemical (e.g. reactant, reagent, solvent, solute), biochemical (e.g. biochemical macromolecules, e.g. DNA, DNA constituents; pharmaceutical active ingredients) or biomedical (blood, serum, cell medium) substances;

storing the sample, in particular for a period of time defined in a programme-controlled manner, in particular under specific physical conditions, e.g. at a specific temperature, temperatures or temperature changes, in particular repeated temperature changes, e.g. cyclic and/or periodically repeated temperature changes and/or setting a surrounding pressure, e.g. applying positive pressure or negative pressure, in particular a vacuum, and/or setting a defined surrounding atmosphere, e.g. a protective gas or a specific humidity, under specific radiation conditions, e.g. shielded against visible light, in the dark or under defined irradiation;

measuring or analysing the sample, in particular analysing by means of a non-invasive and/or invasive treatment of the sample, in particular in order to measure at least one or more chemical, physical, biochemical and/or medical properties of the sample, in particular counting of cells by means of a cell counter;

handling of the sample, in particular changing at least one property of the sample, in particular by means of non-invasive and/or invasive treatment of the sample.

This treatment is, in particular, under program control, using at least one program parameter.

In particular, this treatment is brought about in accordance with at least one control parameter which determines the treatment of the laboratory sample by means of the treatment apparatus. A control parameter can set a period of time, a moment in time, a specific sample volume and/or metering volume, a specific sample temperature, etc. A control parameter can relate to the automatic use of a specific transport head, a specific type of transport container, a specific type of sample container, one or more individual samples or of specific positions of these components in the workspace. A control parameter can relate to the treatment of an individual sample or the treatment of a plurality or multiplicity of samples.

A control parameter is preferably selected automatically by the laboratory instrument, in particular the laboratory machine, as a function of at least one program parameter; in particular, it is selected automatically as a function of the program parameters selected by the user. As a result, an advantage for the user is that he does not need to determine all control parameters individually. The user needs no knowledge about the programming of the laboratory instrument. Rather, the control parameters required for the treatment are selected by means of the program parameters entered by the user. As a result, the use of the laboratory instrument is particularly convenient.

A control parameter can also correspond to a program parameter.

The transport of a sample can be transport from a sample container into a transport container and/or from the transport container into a sample container or any other target location. This transport is, in particular, under program control, using at least one program parameter.

The transport container can be e.g. a dispenser container which comprises a movable plunger and an inlet/outlet opening. The plunger generates negative pressure or positive pressure in the dispenser container and thus sucks the sample into the container or re-emits it. This process follows the displacement principle, i.e. the sample to be moved, which is usually liquid and therefore incompressible, is subjected to forced movement by virtue of the volume previously taken up by the sample being moved by the plunger. In general, this plunger is moved, in particular moved under program control, by a movement apparatus which is assigned to the laboratory machine.

The transport container can furthermore be a pipette tip. A pipette tip has an inlet/outlet opening and a second opening. The second opening is coupled to a suction apparatus such that a liquid sample can be sucked (pipetted) from a sample container into the transport container by means of negative pressure. The sample is emitted by ventilating the suction region, by means of gravity and/or positive pressure which e.g. is generated in the pipette tip by means of the second opening.

The transport container preferably consists partly or wholly of plastic. It is preferably a consumable article, which is typically only used for one treatment or a small number of treatment steps of the sample. However, the transport container can also consist partly or wholly of a different material.

The transport of a sample can be a transport of the sample from an initial position to a target position. The initial position may be present if the sample is disposed in a first sample container and the target position of this sample can be the position thereof in a second sample container, into which the sample is transferred. This type of transport is also referred to presently as sample transfer or transfer. In practice, a sample transfer is usually carried out in order to transfer a sample from a storage container, in which, for example, the sample was stored and/or which may, for example, contain a relatively large amount of the sample, into a second sample container, in which the sample is subjected to further treatment. This transport is, in particular, under program control, using at least one program parameter.

The transport container preferably is or can be connected to a transport apparatus of the laboratory machine.

A sample container can be an individual container, in which only a single sample is contained, or it can be a multiple container, in which a plurality of individual containers connected to one another are disposed.

The single container can be an open container or a sealable container. In the case of a sealable container, provision can be made for a covering element, in particular a sealing cap. The covering element can be securely connected to the container, e.g. as a hinged cover or hinged closure cap, or can be used as separate component.

In a multiple container, the plurality of single containers are preferably disposed in a fixed position with respect to one another, in particular disposed in accordance with the crossing points of a grid pattern. This simplifies the automated approach to the positions and, in particular, the individual addressing of samples. A multiple container can be embodied as plate element, in which the individual containers are connected in such a way that they form a plate-shaped arrangement. The individual containers can be embodied as depressions in a plate or can be interconnected by web elements. The plate element can have a frame element, in which the single containers are held. These connections between components can be integral connections, i.e. cohesive connections and/or connections generated by a common injection moulding process, or they can be generated in a force-fit and/or form-fit manner. In particular, the plate element can be a microtiter plate.

Multiple containers can comprise a plurality (2 to 10) of single containers. They can furthermore comprise a multiplicity (more than 10) thereof, typically 12, 16, 24, 32, 48, 64, 96, 384, 1536 single containers. In particular, the multiple container can be a microtiter plate. A microtiter plate can be embodied in accordance with one or more industrial standards, in particular the industrial standards ANSI/SBS 1-2004, ANSI/SBS 2-2004, ANSI/SBS 3-2004, ANSI/SBS 4-2004.

The maximum sample volume that can be held by a transport container or sample container typically lies between 0.01 ml and 100 ml, in particular 10-100 µl, 100-500 µl, 0.5-5 ml, 5-25 ml, 25-50 ml, 50-100 ml, depending on the type of selected transport container or sample vessel.

A sample container can comprise an information region, which can contain information about the sample container or the content thereof. The information region can contain encoded information, e.g. a barcode or QR code or an RFID chip, or information encoded differently. The information can have information for identifying the sample and/or a sample container. The laboratory machine can have an information reader for reading this information and preferably providing said information to the control apparatus.

The sample container preferably consists partly or wholly of plastic. It is preferably a consumable article, which is typically only used for one treatment or a small number of treatment steps of the sample. However, the sample container can also consist partly or wholly of a different material; by way of example, a storage container, in particular a storage box, can also consist of cardboard.

The sample container preferably can be transported by a transport apparatus of the laboratory machine.

The laboratory instrument, in particular the laboratory machine, is preferably embodied to treat a multiplicity of samples in succession and/or in parallel. In particular, the laboratory machine is preferably embodied to treat, in particular to transport, to empty and/or to fill, a multiplicity of sample vessels, in particular single containers and/or multiple containers, in a program-controlled manner.

Preferably, the laboratory instrument, in particular the laboratory machine, comprises at least one holding apparatus for at least one sample container, in particular a holding frame for holding a plurality of single containers, referred to as "sample vessel rack". The holding apparatus preferably has a transportable embodiment in order to be movable within the workspace of the laboratory machine or between different workspaces. A plurality or multiplicity of individual containers can be held at a predetermined position of the holding apparatus by means of the holding apparatus. As a result, the individual pro-gram-controlled approach or addressing of the sample containers or samples is simplified.

The laboratory instrument, in particular laboratory machine, can comprise a plurality of specialized laboratory instruments, in particular in such a way that it is embodied as a laboratory line, in which a plurality of workspaces are disposed next one another in such a way that, by means of transport device, a single, a plurality or a multiplicity of samples can be transported successively and/or in parallel between the workspaces. A workspace of a laboratory line is preferably embodied in such a way that a specific laboratory object, usually relating to the parallel and/or sequential treatment of a multiplicity of samples, is carried out. At least one laboratory instrument or at least one specific treatment apparatus is preferably provided in a workspace. A high work throughput of the laboratory line is obtained as a result of this specialization of each workspace. In order to perform such a specific object, provision can be made for only one type of treatment of at least one sample or for only a few types of treatment, e.g. two to ten treatment types, to be performed in each workspace. A treatment apparatus for performing a treatment, which is characteristic for a specific laboratory instrument, as described within the scope of the description of the invention, can be disposed at each workstation. The transport device can comprise a guide-rail system and/or a robotic apparatus for program-controlled movement of samples or sample containers.

A laboratory instrument, in particular a laboratory machine, can be connected or connectable to an LIMS. LIMS is an abbreviation for laboratory information and management system. As usual, an LIMS is a software system which relates to data processing in an automated or partly automated chemical, physical, biological or medical laboratory. Such data can originate from measurements of the samples and/or relate to the control of the data handling. An LIMS preferably serves for measurement value acquisition and measurement value evaluation. LIMS is used to increase the work throughput in a laboratory and/or to optimize the efficiency of the treatment of laboratory samples.

A tool element can be e.g. a transport head for the fluid transfer, in particular a pipetting head, which can comprise a connection section for connecting one pipette tip (single channel pipetting head) or for connecting a plurality of pipette tips (multiple channel pipetting head). Liquid can be sucked into the at least one pipette tip if the latter is connected to the connection section by means of at least one pressure and gas-tight channel connected to the pipetting head. In the laboratory machine, this pipetting is performed, in particular, in a program-controlled manner; in particular, it is influenced by at least one program parameter. The transport head can also be a dispensing head which has at least one movement apparatus for moving a plunger of the dispenser tip. In the laboratory machine, the movement apparatus is moved, in particular, in a program-controlled manner; in particular, it is influenced by at least one program parameter. The transport head can serve for metering liquid, in particular for metering in different regions; a transport head can be embodied for metering a liquid sample with a volume that can be selected from a volume range specific to this transport head: e.g. 1-50 µL or 20-300 µL or 50-1000 µL, ("l" and "L" are each an abbreviation for litre). A transport head can be embodied as a single-channel head, in which only one sample is transported, or it can be embodied as a multi-channel head, in particular an eight-channel head or a 12-channel head, in which a plurality of samples are handled or transported in parallel. Preferably, provision is made for specific transport containers, which can be used depending on the respective type of transport head, in particular in accordance with the corresponding volume range.

A tool element can be e.g. a transport head for transporting objects, for example a carrier and/or gripper tool for carrying and/or gripping an object. A carrying tool can comprise a fastening section for detachably fastening the object to the carrying tool, e.g. by a force-fit and/or cohesive and/or magnetic connection between the object and the carrying tool. In this manner, it is possible within the work top or between a plurality of workspaces and/or work tops.

A tool element can furthermore be a treatment unit, e.g. for performing a thermal, acoustic, optical and/or mechanical treatment of at least one sample.

A treatment unit for thermal treatment may comprise a temperature control apparatus in order to set the at least one sample, simultaneously or in succession, to specific temperatures in particular within set periods of times, and/or to change these temperatures with specific rates. This thermal treatment is, in particular, under program control, using at least one program parameter. In this manner, it is possible to perform a PCR (polymerase chain reaction) on e.g. a single, plurality of or a multiplicity of PCR samples.

The laboratory machine may comprise a transport apparatus for transporting at least one movable head section. The head section can be a transport head for transporting at least one sample and/or for transporting at least one tool element. The head section can comprise a connection section for connecting at least one transport container to the transport apparatus.

The transport apparatus can furthermore comprise a program-controlled movement apparatus, also referred to as a robotic apparatus, in order to move the head section and/or the connection section and, in particular, where necessary, the at least one transport container in a program-controlled manner, in particular in accordance with a motion sequence predetermined by the control apparatus or a different control apparatus. This connection section can be provided on this head section. Furthermore, the connection section for connecting a tool element to the head section can be provided on this head section.

The robotic apparatus can comprise one or more drive apparatuses, e.g. electric motors, in order to enable the program-controlled movement of movable components, e.g. of a movable head section, in particular of a holding or gripper tool or of a different movable tool element, e.g. a movable treatment unit. The robotic apparatus can comprise a single member or multi-member movement arm, by means of which the transport of the head section, and, in particular, the transport of samples, is possible between different, preferably freely selectable, positions in the workspace. The robotic apparatus can furthermore comprise a guide-rail system, wherein the head section in this case is fastened to a movable slider or roller element which can be moved by means of this guide-rail system to the positions which are predetermined by the arrangement of the guide-rail system. The movements of the robotic apparatus are preferably controlled by a program, and, in particular, controlled by at least one program parameter.

The laboratory instrument, in particular the laboratory machine, can comprise an information reader in order to read information regarding a sample and/or a sample container and/or a treatment instruction for this sample and/or this sample container and, preferably, make this available to the control apparatus of the laboratory machine.

The laboratory instrument, in particular the laboratory machine, preferably comprises at least one timer apparatus and/or preferably at least one timing apparatus in order to enable the time-dependent treatment of the samples. The time-dependent treatment is preferably controlled by a program, and, in particular, controlled by at least one program parameter.

In a preferred configuration of the laboratory instrument according to the invention, in particular of the laboratory machine, the former is configured, as a function of the treatment type selected by the user and the program parameters entered by the user, to select automatically one or more the following components for use in the program-controlled treatment:

at least one suitable sample container, in particular suitable for holding a plurality of samples which are to be handled together, e.g. which are intended to be mixed or between which a chemical reaction or biochemical, biological or biomedical interaction is intended to occur;

at least one suitable transport container, in particular a pipette tip and/or a dispenser tip;

at least one suitable transport head, to which the preferably automatically selected transport container can be connected, at least one suitable tool element, which serves for performing the desired treatment.

Preferably, the laboratory instrument according to the invention, in particular the laboratory machine, is configured, as a function of the treatment type selected by the user and the program parameters entered by the user, to select automatically one or more the following control parameters for use in the program-controlled treatment:

at least one period of time, during which a specific work step of the treatment is performed;

at least one sample volume and/or metering volume;

at least one work position of the at least one work top;

movement parameters for setting the motion sequence of the robotic apparatus of the laboratory machine required for the desired treatment of the sample.

The laboratory instrument preferably comprises a user interface apparatus for the manual entry of data by a user and for displaying information, in particular information contained in this data, wherein the user interface apparatus comprises an indication apparatus, in particular a display, in particular a touchscreen display.

The laboratory instrument according to the invention can comprise a plurality of treatment apparatuses. The access control device according to the invention can be assigned to a plurality of laboratory instruments according to the invention, in particular connectable or connected thereto by means of a second interface apparatus and, in particular, second data connections. As a result, one access control device can enable the access of the users to more than one laboratory instrument or to a laboratory instrument with more than one treatment apparatus.

A laboratory instrument according to the invention is preferably capable to work independently, i.e. as a stand-alone instrument, which means it may require some user input but does not require a data connection with a further device, e.g. a central control computer, in order to work in a conventional operating mode. The conventional operating mode of the laboratory instrument provides the treatment of the at least one laboratory sample using its treatment apparatus.

The invention furthermore relates to a method for the instrument-controlled treatment of at least one laboratory sample using at least one consumable in a laboratory instrument according to the invention, wherein the following steps are performed by means of the control apparatus of the laboratory instrument: —acquiring, during at least one treatment performed by the treatment apparatus, at least one first item of information dependent on this treatment in first data, in particular by means of a counting or measuring process, —storing at least some of the first data in the storage apparatus; —preferably: transmitting a communication request to the at least one external data processing apparatus and preferably: establishing a remote data connection to an external data processing apparatus via the communication apparatus; —preferably: transmitting at least some of the first data to an external data processing apparatus via the communication apparatus.

Further possible preferred configurations of the method according to the invention can be derived from the description of the laboratory instrument according to the invention and of the system according to the invention and from the preferred configurations thereof.

Further preferred configurations of the laboratory instrument according to the invention and of the system and of the method according to the invention emerge from the following description of the exemplary embodiments in conjunction with the figures and the description thereof. If nothing else is described or if nothing else emerges from the context, the same components of the exemplary embodiments are substantially characterized by the same reference signs. In detail:

FIG. 3a shows an application example of the system according to the invention.

FIG. 3b shows a further application example of the system according to the invention.

Figure 1:
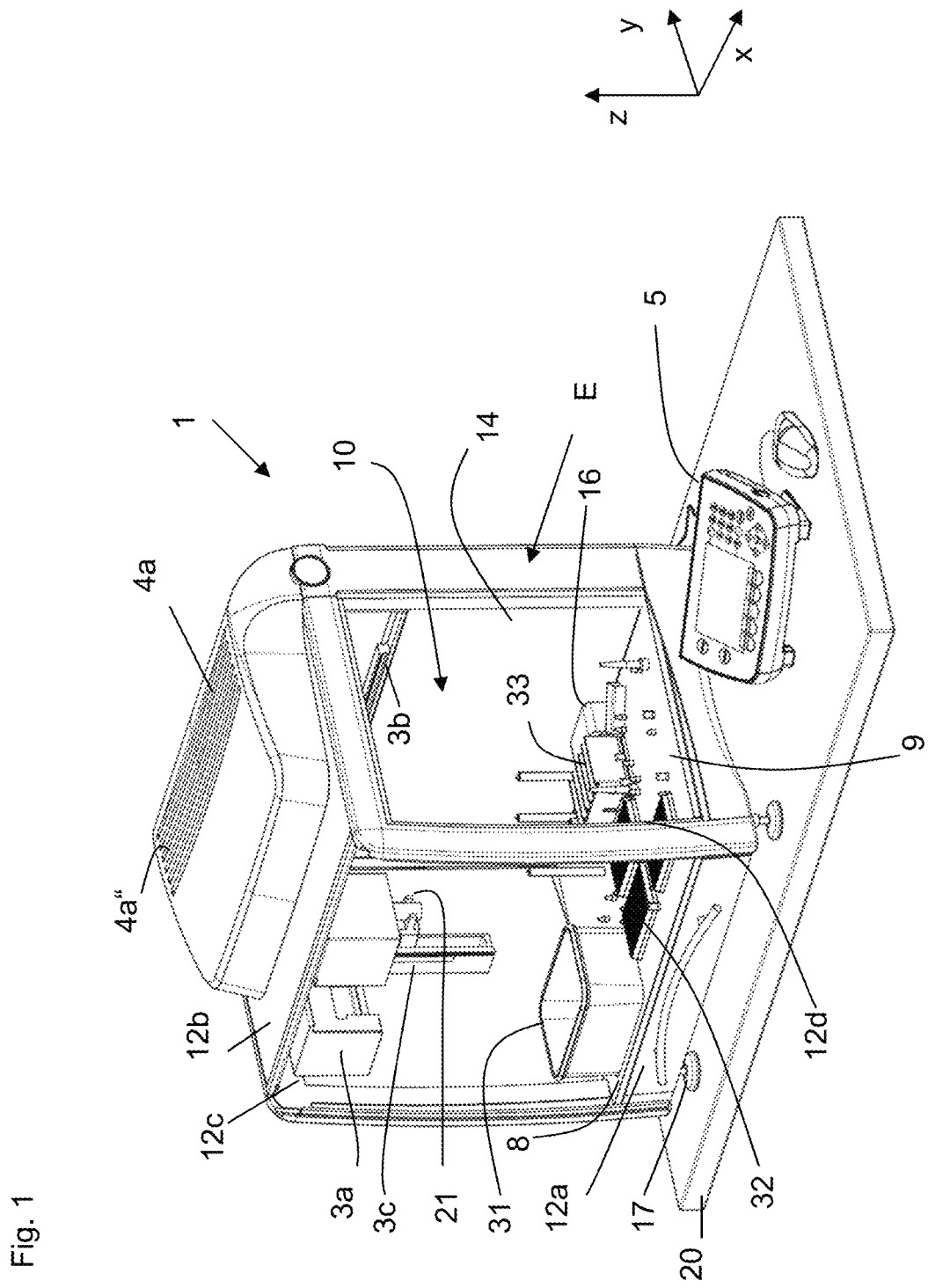
FIG. 1 shows an exemplary embodiment of the laboratory instrument according to the invention.

FIG. 1 shows the laboratory instrument 1, which is embodied here as a laboratory machine 1 for treating fluid samples, to be precise as a pipetting machine. The laboratory machine 1 serves for the program-controlled treatment of these samples.

FIG. 1 shows the laboratory machine 1 for automated processing of liquid samples, in particular for the program-controlled treatment of liquid samples. The laboratory machine 1 is a table-top instrument and disposed on the work table 20 with the four feet 17 thereof. It comprises an electronic control apparatus 2 (not shown here), which is suitable for processing program code for the program-controlled treatment of the liquid samples. The control apparatus 2 is attached in the control space, which is denoted by the arrow E and separated from the workspace 10 by a vertical wall 14. The control space also harbours the voltage supply components which supply the suitable supply voltage for the electrical components of the laboratory machine. The control apparatus 103 of the configuration control device 100 from FIG. 1 is integrated into the control apparatus 2.

The laboratory machine 1 comprises a treatment space 10 for receiving the liquid samples to be treated, a sample handling apparatus 3, controllable in a program-controlled manner, for performing at least one program-controlled treatment step on the at least one sample, which is disposed in the handling space. The components 3a, 3b and 3c of the movement apparatus are assigned to the sample handling apparatus 3.

The laboratory machine 1 comprises a housing 12 comprising a front side 12a, a rear side 12f (not shown here) disposed opposite to the front side, a top side 12b, a bottom side 12e (not shown here) disposed opposite to the top side and two lateral sides 12c and 12d lying opposite one another. The sides 12a, 12b and 12c are substantially made of a material transparent to visible light.

The front side 12a, which is substantially embodied like door 12a, namely a sliding door 12a, can be moved by hand and/or moved in a program-controlled manner and can close downward, substantially along the z-axis of the Cartesian coordinate system. FIG. 2a shows the closed position of the door 12a.

The treatment space 10 is delimited by the front side 12a and the two side faces 12c and 12d, as well as the wall 14 and the worktop 8, which forms the upper side of the base plate 9. The worktop 8 provides six handling stations. The handling stations are substantially planar areas in the handling region 8. Pins serve to align the lab-ware, that is to say the thermorack 33, microtitre plates 32 and waste container 31, at the respective handling station. The exact positioning enables precise, robot-controlled addressing of the sample containers, in particular of the depressions in the microtitre plates 32. A magnetic separation device 16 is disposed in the vicinity of the wall 14, where a thermorack 33, i.e. a temperature-controlled sample vessel holder, is disposed. The magnetic fork (not shown here) of the magnetic separation device 16 enters corresponding receiving channels of the thermorack from the side in order to develop the magnetic effect thereof laterally on the laboratory vessels (sample tubules).

The laboratory machine 1 comprises two decontamination apparatuses, an electronically controllable air purification device for purifying the air in the treatment space, which is controlled electronically and digitally by the control apparatus and which comprises a ventilating device 4a, 4a". The ventilation device comprises three ventilators (not depicted here), which transport an air flow from outside of the device into the treatment space.

The control apparatus 2 comprises a control program. The laboratory machine 1 comprises a sample handling apparatus 3, which comprises a movement apparatus with three guide-rail elements 3a, 3b, 3c, which correspond to movements along the y, x and z-axis of the Cartesian coordinate system. Electronically regulable linear motors are provided for driving the movement along the desired direction. In this manner, the assembly head 21 can be moved into each desired position accessible in the handling space 10. The movement apparatus is part of a robotic system of the sample handling apparatus 3. The assembly head 21 can be transported thereby in a program-controlled manner. A tool instrument, e.g. a pipetting head or a gripper, is connectable to the assembly head. The components disposed in the treatment space, in particular the sample handling apparatus 3, are components of the treatment device of the laboratory machine.

The laboratory machine is configured to undertake equipping of the pipetting head with pipette tips in an automatic and program-controlled manner. The user can at least partly influence this by the programming of a corresponding process program, which controls the progress of the treatment. Therefore, the consumption of consumables, in this case pipette tips, will occur in a program-controlled manner, wherein the user can influence the consumption by his setting of user parameters. By way of example, the user can, when necessary, as a function of the intermediate step of the treatment, set that a new pipette tip or the same pipette tip is used during each transport process for transporting samples from a first microtitre plate into a second microtitre plate. Thus, when the treatment is performed, the consumption of consumables emerges, in particular, from the time when the user starts the treatment. The consumption value can still change during the started treatment as well, for example if a relatively large amount of consumables is required during a subsequent serial dilution after the automatic measurement of a sample concentration.

During the treatment, the control apparatus of the laboratory machine counts the used up pipettes during each program-controlled release of a pipette tips into the disposal container 31 and stores this number as first data in a storage apparatus of the control apparatus. The amount of consumed consumables is fixed at the end of the treatment. This amount of consumed consumables is provided as first data in the storage apparatus in order to transmit the first data to an external data processing apparatus via the communication apparatus (not shown here) of the laboratory instrument, which can be a component of the control apparatus. The external data processing apparatus can be an external data processing apparatus belonging to the system, in particular a computer in the laboratory, an external computer in an intranet of the company or an external computer, which is not a component of the system according to the invention and can be connected via the Internet.

The laboratory machine comprises a user interface apparatus 5, by means of which the user can log onto the laboratory machine locally. It is also possible that the user logs onto a server 90 of an intranet via the user interface apparatus 5. He is then identified by the access control device, which can be a component of the server 90 or a component of the laboratory instrument. Therefore, the system or the laboratory instrument can acquire the consumption of consumables in a user-dependent manner and second data can, as a function of the user, be transmitted for the user to the laboratory instrument, in particular as user-dependent product information.

Figure 2:
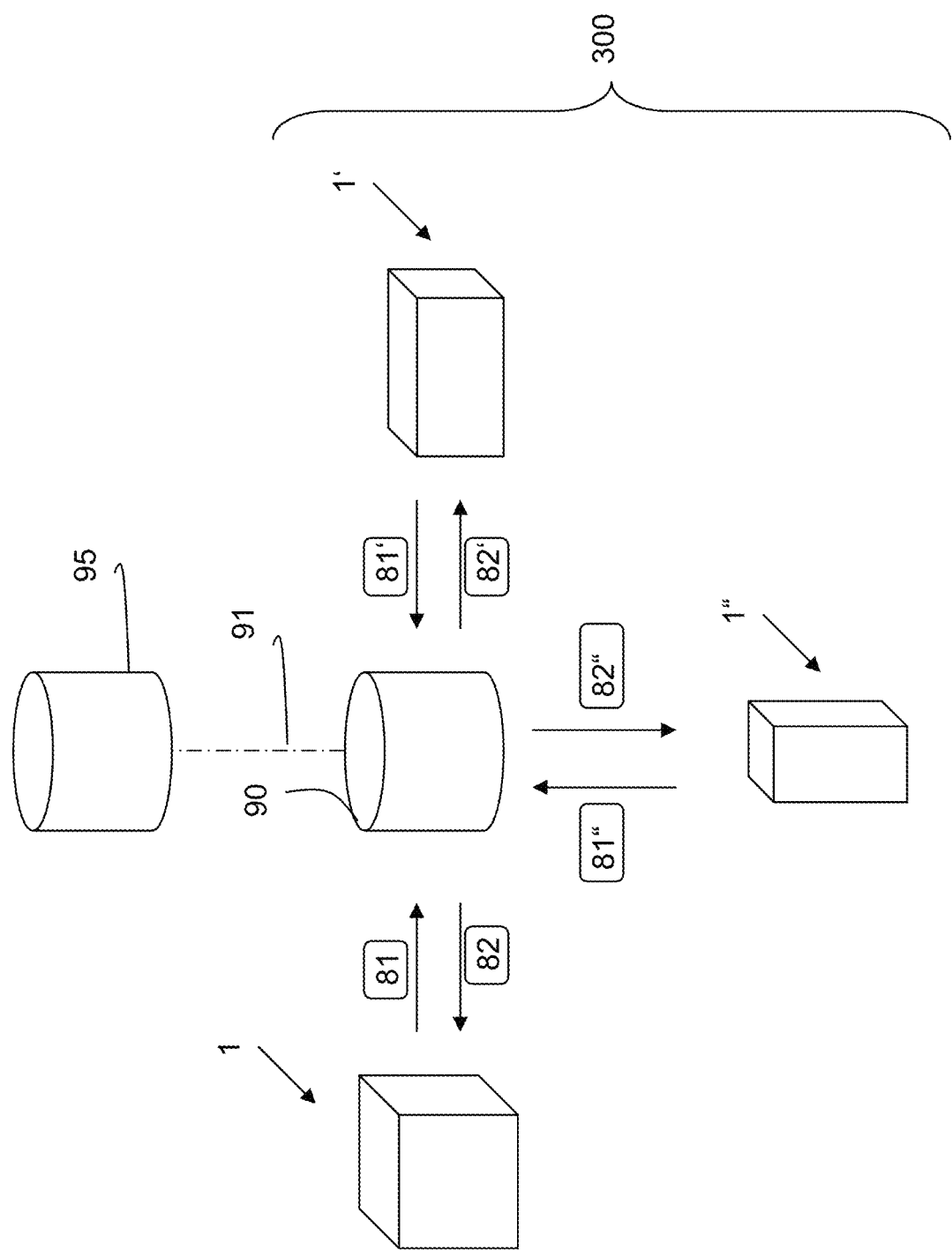
FIG. 2 shows an exemplary embodiment of the system according to the invention.

FIG. 2 shows an exemplary embodiment 300 of the system according to the invention. The system comprises the external data processing apparatus 90 belonging to the system, which is a server 90 that is or can be connected via an intranet to various laboratory instruments 1, 1' and 1" according to the invention. The server 90 comprises a communication apparatus with which the remote data connection to the laboratory instruments can be established and, moreover, the remote data connection 91 to a second external server 95 can be realized or established. The remote data connection 91 to the second external server 95 is realized via the Internet. The second external server 95 is external to the system 300; here, it is not provided as a component of the system 300. However, this would likewise be possible.

Each laboratory instrument 1, 1', 1" of the system 300 is configured to acquire, buffer store and transmit to the server 90 first data 81, 81', 81" about the used consumables during the performed treatments, which server can store said data in the storage apparatus thereof and process them. The server 90 can process these data to form further first data about the used consumables; in particular, it is possible for the server to combine the first data about specific consumables for a plurality of different or similar laboratory instruments. The first server 90 can initiate a data connection to a second external server 95. This process can also be initiated by a further external server 93, which can be a component of the system 300 and which can be assigned to e.g. a purchasing division of the company operating the system 300 in the application of the system 300.

The application example in FIG. 3a schematically shows the application of the system 300 as an automated ordering system for consumables.

Preferably, in this case, the external server 90 of the system comprises a planning apparatus in order, in particular, to determine at least one statistical variable about used consumables. This statistical variable can be a sum of consumables in relation to a specific reference variable, e.g. the type of treatment. The planning apparatus can take account of booking data in a booking database, which can be a component of the server 90, in order to determine first data and, in particular, to transmit these first data to the Internet server 95, which, in one application example of the system 300, can be assigned to a provider of information and products, in particular to a seller of consumable material. The second external server 95 can return, as second data, e.g. a confirmation to the server 90 about receipt of the first data, which the server 90 then receives as second data. Moreover, a laboratory instrument 1, 1' and/or 1" can be configured to receive "push" information as second data 82, 82' and/or 82", which are transmitted by the Internet server 95, via a previously agreed information channel.

A laboratory instrument 1, 1' and/or 1" can indicate this information, in particular automatically, on the indication apparatus of the user interface apparatus 5, i.e. without the system, in which this information channel is shared, having any further influence. This application example of the system 300 is shown in FIG. 3b. Second data are transmitted by the server 95 in accordance with "push technology" directly to the laboratory instrument, in each case via the opened information channel, in order to indicate information to a respective user. It is also possible to transmit maintenance information in addition to information about consumables. In particular, first data can also contain information about the wear of components of the laboratory instrument, which are forwarded as first data to the external server 95 and as a response to which the server 95 reacts with the transmission of second data, in particular by means of "push" data transmission.

Figure 4:
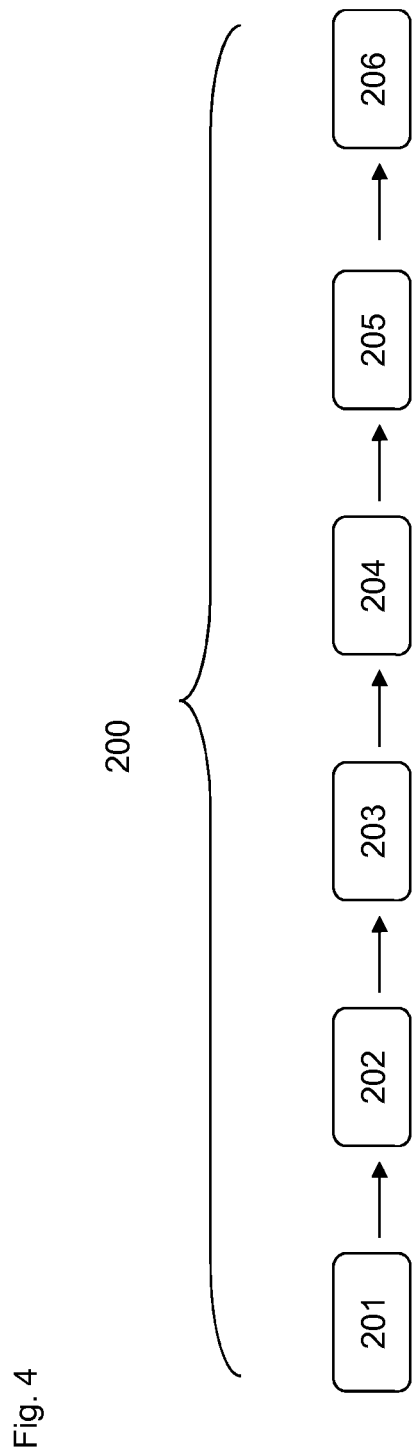
FIG. 4 shows an exemplary embodiment of the method according to the invention.

An exemplary embodiment shown in FIG. 4 of the method 200 according to the invention is a method for the instrument-controlled treatment of at least one laboratory sample using at least one consumable in a laboratory instrument according to the invention, wherein the following steps are performed by means of the control apparatus:

acquiring, during at least one treatment performed by a treatment apparatus, at least one first item of information dependent on this treatment in first data, in particular by means of a counting or measuring process (step 201);

storing at least some of the first data in the storage apparatus (202);

transmitting a communication request to the at least one external data processing apparatus (203)

establishing a remote data connection to an external data processing apparatus via the communication apparatus (204);

transmitting at least some of the first data via the communication apparatus to an external data processing apparatus (204), which, in particular, can be a component of the system according to the invention;

receiving second data via the communication apparatus (205), in particular by means of "push technology"

processing the second data and indicating information obtained from the second data on an indication apparatus of the user interface apparatus (206).

Figure 5:
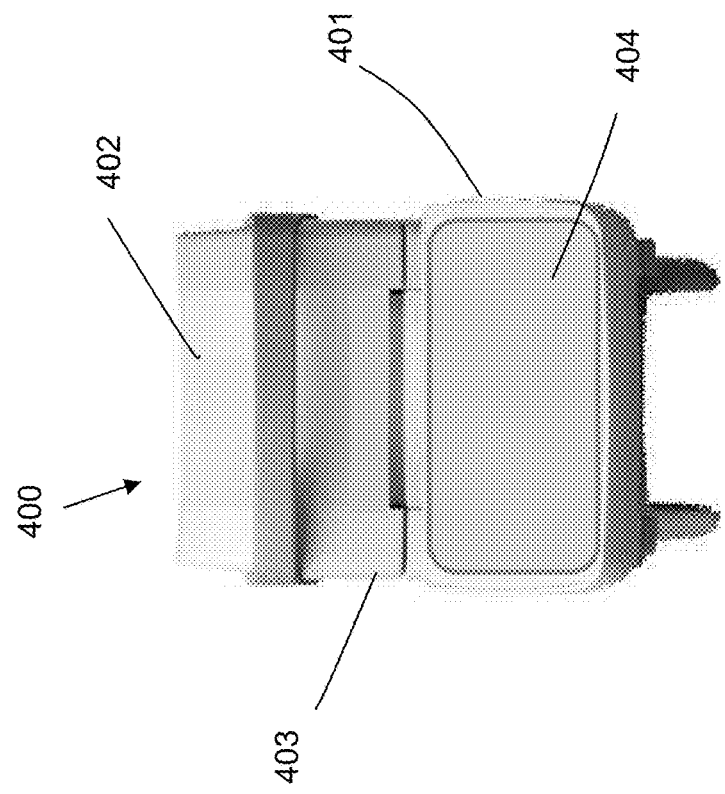
FIG. 5 shows a further exemplary embodiment of the laboratory instrument according to the invention, in this case a thermocycler.

FIG. 5 shows a laboratory instrument 400, a thermocycler, embodied for automated processing of liquid samples, in particular for the program-controlled temperature control of liquid samples. The laboratory instrument 400 is a tabletop instrument. It comprises an integrated electronic control apparatus 406 (not shown here), which is suitable for processing program code for the program-controlled treatment of the liquid samples. The control apparatus 406 is housed in the housing 401. The housing also harbours the voltage supply components which supply the suitable supply voltage for the electrical components of the thermocycler.

The laboratory instrument 400 comprises a treatment space 403 for receiving the liquid samples to be treated, which can hold at least one treatment apparatus 408 (not shown here), controllable in a program-controlled manner, for performing at least one program-controlled treatment step on the at least one sample, which is disposed in the treatment apparatus disposed in the handling space. The treatment space can be sealed by a cover 402 in order to establish defined temperature-control surroundings. In FIG. 5, the laboratory instrument is depicted in the closed state.

The control apparatus 103 of the access control device 100 from FIG. 1 is integrated into the control apparatus 406. The control apparatus 406 comprises a control program.

The laboratory instrument comprises a user interface apparatus 404, by means of which a user can log onto the laboratory instrument locally. The laboratory instrument 400 can store and, by means of the communication apparatus thereof, transmit to the external data processing apparatus first data relating to used consumable material, in particular as a function of the logged-on user.

The control apparatus 406 is configured to acquire, in particular by means of a counting process, at least a first item of information, dependent on this treatment, in first data during at least one treatment performed by the treatment apparatus and to store at least some of the first data in the storage apparatus, wherein the laboratory instrument comprises a communication apparatus for establishing a data connection to at least one external data processing apparatus, wherein the communication apparatus is configured to transmit these at least some first data to the—in particular second—external data processing apparatus. The counting process can count the removal and/or insertion of a multiple-sample container, in particular a microtitre plate, from/into the treatment space 403. Each counted process can then be classified as consumption of a multiple sample container and this information can be collected and/or transmitted as first data to the—in particular second—external communication apparatus.

Figure 6:
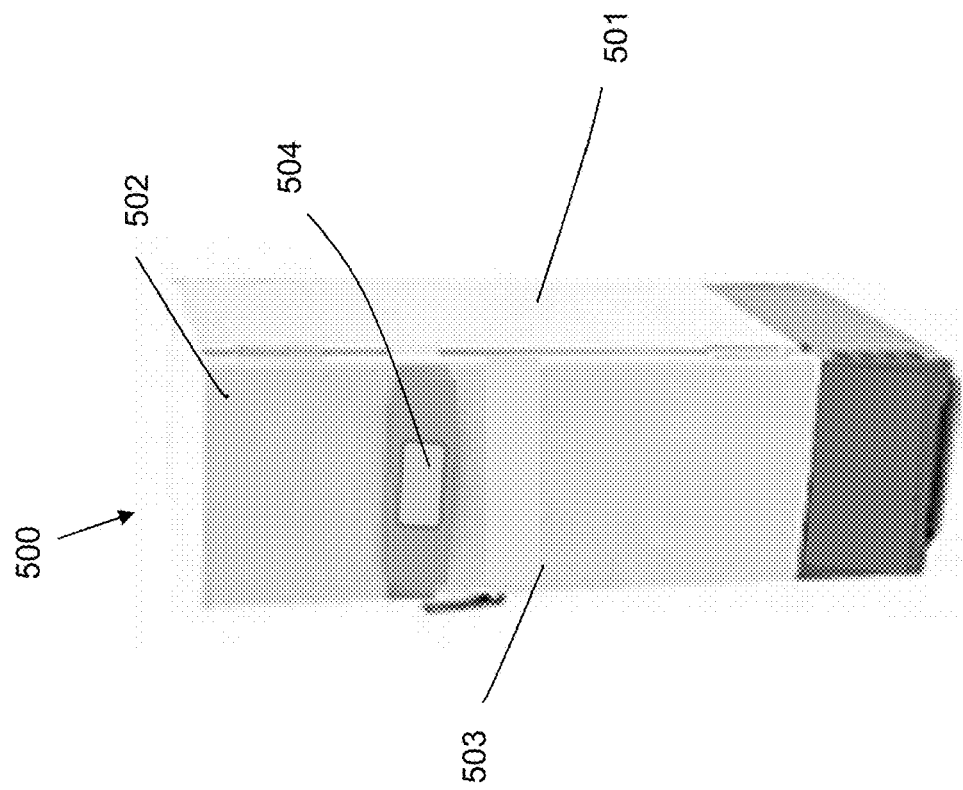
FIG. 6 shows a further exemplary embodiment of the laboratory instrument according to the invention, in this case a laboratory freezer.

FIG. 6 shows, in a further exemplary embodiment of the invention, a laboratory instrument 500, a laboratory freezer, for storing laboratory samples, in particular at temperatures under −50° C. The laboratory instrument 500 is a tabletop instrument. It comprises an integrated electronic control apparatus 506 (not shown here), which is suitable for setting, regulating and monitoring the temperature in the required range. The control apparatus 506 is housed in the housing 501. The housing also harbours the voltage supply components which supply the suitable supply voltage for the electrical components of the laboratory freezer.

The laboratory instrument 500 comprises a treatment space 503 for holding the samples to be stored, comprising at least one program-controlled controllable treatment apparatus 408 (not shown here) which, in the case of the laboratory freezer, corresponds to a sealed region with a defined adjustable temperature. Here, the program-controlled treatment step corresponds to freezing the at least one sample, which is disposed in the treatment apparatus disposed in the handling space. The treatment space can be sealed by a door 502 in order to establish defined temperature-control surroundings. In the case of more than one treatment apparatus, a plurality of doors, optionally disposed behind the common door 502, are also conceivable. In FIG. 5, the laboratory instrument is depicted in the closed state.

The control apparatus 103 of the access control device 100 from FIG. 1 is integrated into the control apparatus 506 of the laboratory instrument 500. The control apparatus 406 comprises a control program.

The laboratory instrument comprises a user interface apparatus 504, by means of which a user can log onto the laboratory instrument locally.

The control apparatus 506 is configured to acquire, in particular by means of a counting process, at least a first item of information, dependent on this treatment, in first data during at least one treatment performed by the treatment apparatus and to store at least some of the first data in the storage apparatus, wherein the laboratory instrument comprises a communication apparatus for establishing data connection to at least one external data processing apparatus, wherein the communication apparatus is configured to transmit these at least some first data to the—in particular second—external data processing apparatus. The counting process can count the removal and/or insertion of a multiple-sample container, in particular a microtitre plate, from/into the treatment space 503. Each counted process can then be classified as consumption of a multiple sample container and this information can be collected and/or transmitted as first data to the—in particular second—external communication apparatus.

The invention claimed is:

1. A laboratory instrument for the instrument-controlled treatment of at least one fluid laboratory sample, comprising:
at least one treatment apparatus, which is configured to perform the treatment of the at least one fluid laboratory sample by way of a pipetting process using an amount of at least one consumable being a container manufactured from plastic or comprising plastic, and
a control apparatus for controlling the treatment, comprising a data processing apparatus and a storage apparatus for storing data,
wherein the control apparatus is configured:
to acquire, during at least one treatment performed by a treatment apparatus, at least one first item of information dependent on this treatment in first data, in particular by means of a counting, measuring or calculating process, wherein the control apparatus is configured to acquire the first data as a function of a type of treatment using the pipetting process and the at least one consumable, and
to store at least some of the first data in the storage apparatus,
wherein the laboratory instrument comprises a communication apparatus for establishing a data connection to at least one external data processing apparatus,
wherein the communication apparatus is configured to transmit these at least some first data to the external data processing apparatus, and
wherein the communication apparatus is configured to receive a communication request, which was initiated by the external data processing apparatus and transmitted from the external data processing apparatus to the communication apparatus,
wherein the communication apparatus is configured to automatically permit a remote data connection on the basis of the communication request, said remote data connection initiated by the external data processing apparatus being established between the external data processing apparatus and the communication apparatus,
wherein the remote data connection is an internet-based type of communication between the external data processing apparatus and the communication apparatus, wherein upon a preceding agreement between the external data processing apparatus and the communication apparatus, an information channel is opened to directly transmit push information as second data to the communication apparatus using push technology,
the laboratory instrument comprising a user interface apparatus with an indication apparatus,
wherein the control apparatus is configured to process the second data automatically and to obtain second items of push information from the second data and to indicate these second items of information to the user on the indication apparatus of the user interface apparatus.

2. The laboratory instrument according to claim 1, wherein the control apparatus is configured to control the communication request from the external data processing apparatus, in particular to permit the remote data connection, as a function of the first data and/or as a function of other conditions.

3. The laboratory instrument according to claim 1, comprising an access control device configured to control the access, in particular the communication request, of the external data processing apparatus.

4. The laboratory instrument according to claim 1, wherein the control apparatus is configured:
to acquire, during at least one treatment, at least one first item of information about the variable X as a function of Y, in particular by counting or measuring, wherein the values X and Y characterize at least one consumable Y of the amount X, and to acquire this at least one first item of information in the first data.

5. The laboratory instrument according to claim 1, comprising
a user interface apparatus and
an access control device, which is configured to control, in particular permit, the access of at least one user accessing via the user interface apparatus and to identify this user in the process,
wherein the control apparatus is configured to acquire the first data as a function of the identified user and/or to acquire the information relating to the identified user as a component of the first data.

6. The laboratory instrument according to claim 1, wherein the control apparatus is configured to establish, in particular calculate, the first data as a function of at least one planned treatment, in particular as a function of at least one treatment planned in accordance with the booking data from a booking database.

7. The laboratory instrument according to claim 1, comprising a planning apparatus for planning an expected consumption of consumables, wherein the control apparatus is configured to transmit this demand for consumables to be expected as "first data" to the external data processing apparatus.

8. A method for the instrument-controlled treatment of at least one fluid laboratory sample by way of a pipetting process using at least one consumable in a laboratory instrument according to claim 1, said method comprising:
acquiring, during at least one treatment performed by the treatment apparatus, at least one first item of information dependent on this treatment in first data, in particular by means of a counting or measuring process,
storing at least some of the first data in the storage apparatus;

transmitting at least some of the first data to an external data processing apparatus via the communication apparatus; wherein said acquiring, storing, and transmitting are performed by means of the control apparatus, and acquiring the first data additionally as a function of a type of treatment of the at least one fluid laboratory sample using a pipetting process.

* * * * *